(12) United States Patent
Kubik et al.

(10) Patent No.: US 9,596,871 B2
(45) Date of Patent: Mar. 21, 2017

(54) CANOLA GERMPLASM EXHIBITING SEED COMPOSITIONAL ATTRIBUTES THAT DELIVER ENHANCED CANOLA MEAL NUTRITIONAL VALUE

(75) Inventors: Thomas J. Kubik, Saskatoon (CA); Gregory R. Gingera, Saskatoon (CA); Van L. Ripley, Grandora (CA); Michelle E. Beaith, Saskatoon (CA); Thomas G. Patterson, Westfield, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 1165 days.

(21) Appl. No.: 13/401,752

(22) Filed: Feb. 21, 2012

(65) Prior Publication Data

US 2012/0216307 A1 Aug. 23, 2012

Related U.S. Application Data

(60) Provisional application No. 61/445,426, filed on Feb. 22, 2011.

(51) Int. Cl.
*A01H 5/10* (2006.01)

(52) U.S. Cl.
CPC .............. *A23K 10/30* (2016.05); *A01H 5/10* (2013.01); *A23K 50/10* (2016.05); *A23K 50/30* (2016.05); *A23K 50/75* (2016.05); *A23L 25/00* (2016.08)

(58) Field of Classification Search
None
See application file for complete search history.

(56) References Cited

U.S. PATENT DOCUMENTS

| | | | |
|---|---|---|---|
| 4,769,061 A | 9/1988 | Comai | |
| 4,810,648 A | 3/1989 | Stalker | |
| 4,940,835 A | 7/1990 | Shah et al. | |
| 4,975,374 A | 12/1990 | Goodman et al. | |
| 5,266,317 A | 11/1993 | Tomalski et al. | |
| 5,494,813 A | 2/1996 | Hepher et al. | |
| 5,662,958 A | 9/1997 | Kennelly et al. | |
| 5,850,026 A | 12/1998 | DeBonte et al. | |
| 6,248,876 B1 | 6/2001 | Barry et al. | |
| 6,433,254 B1 | 8/2002 | Sernyk | |
| 7,223,577 B2 | 5/2007 | Steward et al. | |
| 7,718,852 B2 | 5/2010 | Chungu et al. | |
| 7,723,578 B2 | 5/2010 | Chungu et al. | |
| 7,723,579 B2 | 5/2010 | Chungu et al. | |
| 7,723,580 B2 | 5/2010 | Chungu et al. | |
| 7,723,581 B2 | 5/2010 | Chungu et al. | |
| 7,723,582 B2 | 5/2010 | Chungu et al. | |
| 7,728,195 B2 | 6/2010 | Chungu et al. | |
| 8,304,611 B2 | 11/2012 | Kubik et al. | |
| 8,304,612 B2 | 11/2012 | Kubik et al. | |
| 8,304,613 B2 | 11/2012 | Kubik et al. | |
| 8,304,614 B2 | 11/2012 | Kubik et al. | |
| 8,324,459 B2 | 12/2012 | Kubik et al. | |
| 8,324,460 B2 | 12/2012 | Chungu et al. | |
| 8,324,461 B2 | 12/2012 | Chungu et al. | |
| 8,367,896 B2 | 2/2013 | Chungu et al. | |
| 8,378,177 B2 | 2/2013 | Chungu et al. | |
| 8,389,811 B2 | 3/2013 | Chungu et al. | |
| 8,519,228 B2 | 8/2013 | Gingera et al. | |
| 8,519,229 B2 | 8/2013 | Gingera et al. | |
| 8,530,726 B2 | 9/2013 | Kubik et al. | |
| 8,541,656 B2 | 9/2013 | Chungu et al. | |
| 8,541,657 B2 | 9/2013 | Ripley et al. | |
| 8,541,658 B2 | 9/2013 | Ripley et al. | |
| 8,558,064 B2 | 10/2013 | Ripley | |
| 8,558,065 B2 | 10/2013 | Kubik et al. | |
| 8,563,810 B2 | 10/2013 | Kubik et al. | |
| 8,563,811 B2 | 10/2013 | Kubik et al. | |
| 8,575,435 B2 | 11/2013 | Gingera et al. | |
| 8,664,477 B2 | 3/2014 | Gingera et al. | |
| 8,669,422 B2 | 3/2014 | Ripley et al. | |

(Continued)

FOREIGN PATENT DOCUMENTS

| CA | 2180386 | 9/2006 |
|---|---|---|
| CN | 101610689 | 7/2008 |

(Continued)

OTHER PUBLICATIONS

Bell, J.M., "Factors affecting the nutritional value of canola meal: A review" Can. J. Anim. Sci. vol. 73, pp. 679-697, 1993.
Hoffman, P. C., "Canola Meal" Univ. of Wisconsin, Cooperative Extension, 1990, 2 pages.
International Search Report for International Application No. PCT/US2012/025981, dated Dec. 21, 2012.
Written Opinion for International Application No. PCT/US2012/025981, dated Dec. 21, 2012.
Rakow, G. et al, "Rapeseed genetic research to improve its agronomic performance and seed quality," HELIA, 2007, pp. 199-206, vol. 30 No. 46.
International Search Report for International Application No. PCT/US2012/025975, dated Nov. 26, 2012.
Written Opinion for International Application No. PCT/US2012/025975, dated Nov. 26, 2012.

(Continued)

*Primary Examiner* — Elizabeth McElwain
(74) *Attorney, Agent, or Firm* — Marcia L. Rosenfeld; Magleby Cataxinos & Greenwood

(57) ABSTRACT

The present invention concerns a canola germplasm comprising at least 45% crude protein and not more than 18% acid detergent fiber content on an oil-free, dry matter basis. Certain embodiments further comprise one or more traits selected from the group consisting of reduced polyphenolic content and increased phosphorous content. In particular embodiments, the invention concerns canola plants comprising such germplasm and plant commodity products (e.g., seeds) produced therefrom. Canola plants comprising a germplasm of the invention may exhibit favorable seed composition characteristics that make them particularly valuable as a source for canola meal, and for methods of introducing at least one trait selected from the group consisting of high protein content, low fiber content, reduced polyphenolic content and increased phosphorous content into a canola variety in a seed coat color-independent manner.

37 Claims, 2 Drawing Sheets

(56) References Cited

U.S. PATENT DOCUMENTS

| | | |
|---|---|---|
| 2002/0124283 A1 | 9/2002 | Facciotti |
| 2008/0260930 A1 | 10/2008 | Chungu et al. |
| 2009/0093367 A1 | 4/2009 | Kubik |
| 2010/0215831 A1 | 8/2010 | Saito et al. |
| 2010/0303999 A1 | 12/2010 | Chungu et al. |
| 2011/0191885 A1 | 8/2011 | Kubik et al. |
| 2012/0174266 A1 | 7/2012 | Kubik et al. |
| 2012/0204286 A1 | 8/2012 | Gingera et al. |
| 2012/0213909 A1 | 8/2012 | Kubik et al. |
| 2012/0216307 A1 | 8/2012 | Kubik et al. |
| 2013/0219539 A1 | 8/2013 | Ripley et al. |
| 2013/0219540 A1 | 8/2013 | Gingera et al. |
| 2013/0219541 A1 | 8/2013 | Gingera et al. |
| 2013/0298279 A1 | 11/2013 | Gingera et al. |

FOREIGN PATENT DOCUMENTS

| | | |
|---|---|---|
| EP | 1915050 | 4/2008 |
| JP | 2009502199 | 1/2009 |
| JP | 2014507161 | 3/2014 |
| JP | 2014507162 | 3/2014 |
| WO | 98-49889 | 11/1998 |
| WO | 2005012515 A2 | 2/2005 |
| WO | 2005107437 A2 | 11/2005 |

OTHER PUBLICATIONS

"Novel Food Information—Food Biotechnology High oleic acid/ low linolenic acid canola lines 45A37, 46A40", FD/OFB-096-228-A, Oct. 1999, 3 pages, http://cera-gmc.org.docs/decdocs/ofb-096-228-a.pdf.

FIG. 1. Sample seeds of exemplary canola varieties
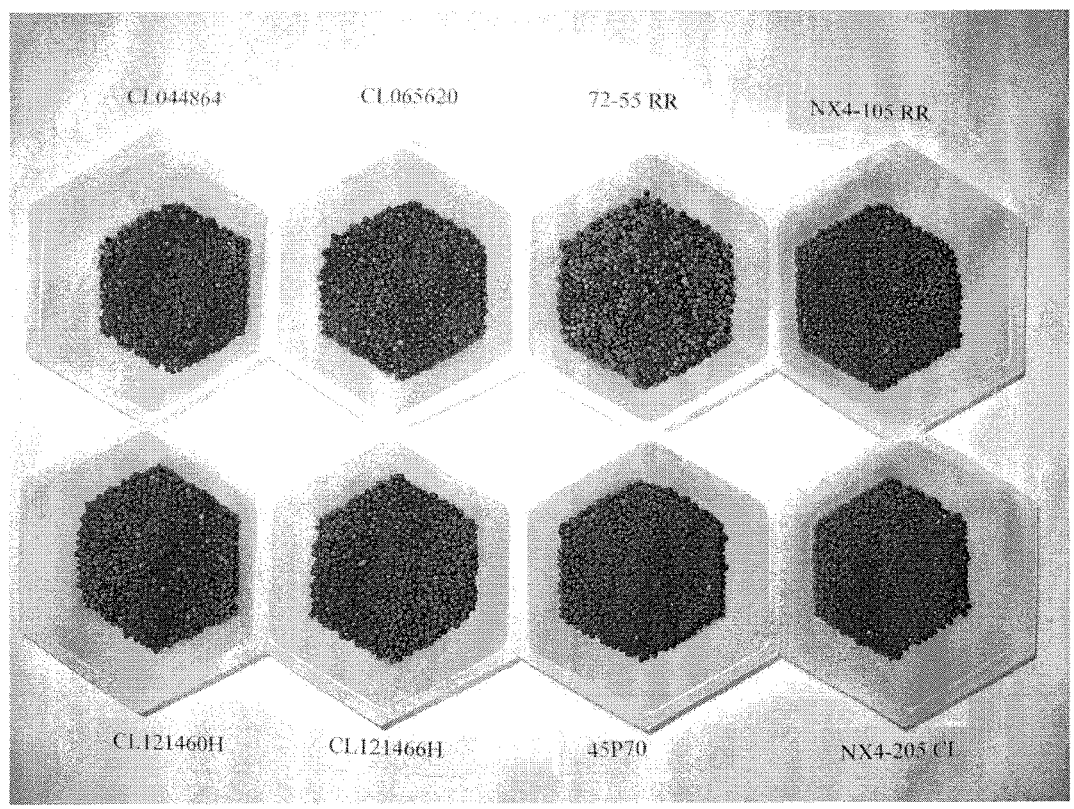

FIG. 2. Composition analysis of seed from field grown samples

| Name | Seed Quality by NIR | | | | Reference Chemistry - 3 locations | | | | |
|---|---|---|---|---|---|---|---|---|---|
| | % Oil Dry Mass NIR | % Meal Protein NIR 10% H₂O | Total Glucosinolate NIR 10% H₂O | % ADF NIR 10% H₂O | % Oil Dry Mass NMR | % Protein 10% H₂O | % ADF 10% H₂O | Condensed Tannin OD 520/g ADF | Condensed Tannin OD 550/g ADF |
| NX4-105 RR | 48.3 | 41.3 | 9.7 | 14.8 | 48.9 | 38.4 | 18.4 | 4.1 | 5.4 |
| 72-55 RR | 50.9 | 41.9 | 12.5 | 11.2 | 50.2 | 40.6 | 12.6 | 0.2 | 0.2 |
| NX4-205 CL | 47.7 | 41.7 | 10.2 | 16.2 | 49.8 | 38.4 | 19.9 | 6.7 | 9.1 |
| 45P70 | 47.1 | 41.1 | 10.5 | 14.2 | 47.6 | 38.5 | 15.6 | 1.6 | 2.1 |
| CL044864 | 48.5 | 44.1 | 10.2 | 12.2 | 48.1 | 42.0 | 12.8 | 0.2 | 0.2 |
| CL065620 | 50.0 | 44.2 | 10.8 | 11.2 | 49.8 | 42.1 | 12.5 | 0.4 | 0.4 |
| CL121460H | 49.2 | 43.2 | 9.9 | 12.2 | 49.3 | 42.1 | 13.5 | 0.3 | 0.3 |
| CL121466H | 48.1 | 43.2 | 9.5 | 13.5 | 47.7 | 42.0 | 15.0 | 0.8 | 1.0 |

72-55RR and 45P70 are commercial canola hybrids sold by Monsanto Company and Pioneer Hi-Bred, respectively.
NX4-105 RR and NX4-205 RR are dark-seeded commercial canola lines sold by Dow AgroSciences, LLC.

CANOLA GERMPLASM EXHIBITING SEED COMPOSITIONAL ATTRIBUTES THAT DELIVER ENHANCED CANOLA MEAL NUTRITIONAL VALUE

CROSS-REFERENCE TO RELATED APPLICATION

This application claims the benefit under 35 U.S.C. §119 (e) of U.S. Provisional Application No. 61/445,426, filed Feb. 22, 2011, which is incorporated in its entirety by reference herein.

FIELD OF THE INVENTION

The present invention relates to canola germplasm and cultivars. In some embodiments, the invention relates to canola germplasm having meal composition attributes (e.g., reduced levels of anti-nutritional factors and increased protein levels) that are modified independently of seed coat color. Particular embodiments relate to canola germplasm demonstrating dark seed color in combination with, for example, reduced levels of anti-nutritional factors (e.g., acid detergent fiber (ADF) and polyphenolic compounds) and increased protein and phosphorous levels.

BACKGROUND OF THE INVENTION

"Canola" refers to rapeseed (*Brassica* spp.) that has an erucic acid (C22:1) content of at most 2 percent by weight (compared to the total fatty acid content of a seed), and that produces (after crushing) an air-dried meal containing less than 30 micromoles (μmol) of glucosinolates per gram of defatted (oil-free) meal. These types of rapeseed are distinguished by their edibility in comparison to more traditional varieties of the species. Canola oil is considered to be a superior edible oil due to its low levels of saturated fatty acids.

Although rapeseed meal is relatively high in protein, its high fiber content decreases its digestibility and its value as an animal feed. Compared to soybean meal, canola and oilseed rape meal contains higher values of dietary fiber and a lower percentage of protein. Because of its high dietary fiber, canola meal has about 20% less metabolizable energy (ME) than soybean meal. As a result, the value of the meal has remained low relative to other oilseed meals such as soybean meal, particularly in rations for pigs and poultry. Rakow (2004a) *Canola meal quality improvement through the breeding of yellow-seeded varieties—an historical perspective*, in *AAFC Sustainable Production Systems Bulletin*. Additionally, the presence of glucosinolates in some canola meals also decreases its value, due to the deleterious effects these compounds have on the growth and reproduction of livestock.

Canola varieties are distinguished in part by their seed coat color. Seed coat color is generally divided into two main classes: yellow and black (or dark brown). Varying shades of these colors, such as reddish brown and yellowish brown, are also observed. Canola varieties with lighter seed coat color have been widely observed to have thinner hulls, and thus less fiber and more oil and protein than varieties with dark color seed coats. Stringam et al. (1974) Chemical and morphological characteristics associated with seed coat color in rapeseed, in *Proceedings of the 4th International Rapeseed Congress*, Giessen, Germany, pp. 99-108; Bell and Shires (1982) Can. J. Animal Science 62:557-65; Shirzadegan and Röbbelen (1985) Götingen Fette Seifen Anstrichmittel 87:235-7; Simbaya et al. (1995) J. Agr. Food Chem. 43:2062-6; Rakow (2004b) *Yellow-seeded Brassica napus canola for the Canadian canola Industry*, in *AAFC Sustainable Production Systems Bulletin*. One possible explanation for this is that the canola plant may expend more energy into the production of proteins and oils if it does not require that energy for the production of seed coat fiber components. Yellow-seeded canola lines also have been reported to have lower glucosinolate content than black-seeded canola lines. Rakow et al. (1999b) Proc. 10th Int. Rapeseed Congress, Canberra, Australia, Sep. 26-29, 1999, Poster #9. Thus, historically the development of yellow-seeded canola varieties has been pursued as a potential way to increase the feed value of canola meal. Bell (1995) *Meal and by-product utilization in animal nutrition, in Brassica oilseeds, production and utilization*. Eds. Kimber and McGregor, Cab International, Wallingford, Oxon, OX108DE, UK, pp. 301-37; Rakow (2004b), supra; Rakow & Raney (2003).

Some yellow-seeded forms of *Brassica* species closely related to *B. napus* (e.g., *B. rapa* and *B. juncea*) have been shown to have lower levels of fiber in their seed and subsequent meal. The development of yellow-seeded *B. napus* germplasm has demonstrated that fiber can be reduced in *B. napus* through the integration of genes controlling seed pigmentation from related *Brassica* species. However, the integration of genes controlling seed pigmentation from related *Brassica* species into valuable oilseed *Brassica* varieties, such as canola varieties, is complicated by the fact that multiple recessive alleles are involved in the inheritance of yellow seed coats in presently available yellow-seeded lines. Moreover, "pod curling" is also a problem commonly encountered during integration of yellow seed coat color from other *Brassica* species, such as *juncea* and *carinata*.

Very little information is available as to how much variability there is for fiber within dark-seeded *B. napus* germplasm, and no reports have been made of dark-seeded canola lines having been developed that contain reduced levels of anti-nutritional factors (e.g., fiberand polyphenolic compounds), and increased protein levels.

BRIEF SUMMARY OF THE INVENTION

Described herein are canola (*Brassica napus*) open pollinated cultivars (CL044864, CL065620) and hybrids (CL166102H, CL121460H and CL121466H) comprising germplasm providing a novel combination of seed color and/or canola meal compositional changes that have been shown to impact nutritional value. In some embodiments, canola plants comprising germplasm of the invention may produce seed with, for example, novel combinations of protein, fiber, and phosphorous levels, such that these seed components are independent of seed coat color. In particular embodiments, such plants may produce seed with higher protein and lower fiber than standard canola types, as well as phosphorous levels that are similar to, or higher than, phosphorous levels in standard canola types. Canola inbred lines and hybrids comprising germplasm of the invention may in some embodiments deliver nutritionally-enhanced meal properties when utilized directly as a feed or food ingredient, and/or when utilized as feed stock for processing protein isolates and concentrates. Such seeds may be dark (e.g., black, dark, and mottled) or light colored.

Thus, described herein is a *Brassica* germplasm that may be used to obtain canola plants having desirable seed component traits in a seed color-independent manner. In some embodiments, plants comprising such a germplasm may be used to produce a canola meal with desirable nutritional qualities. In particular embodiments, inbred canola lines (and plants thereof) comprising a germplasm of the invention are provided. In further embodiments, hybrid canola lines (and plants thereof) having an inbred canola plant comprising a germplasm of the invention as a parent are provided. Canola varieties of the invention include, for example, and without limitation: CL044864; CL065620; CL166102H; CL121460H; and CL121466H.

Also described herein are plant commodity products obtained from inbred canola plants or hybrids comprising a germplasm of the invention. Particular embodiments include a canola meal or seed obtained from such inbred canola plant or hybrid.

Also described are methods for improving the nutritional value of a canola meal. For example, methods are described for introgressing a combination of canola meal compositional characteristics into a *Brassica* germplasm in a seed color-independent manner. In particular embodiments, a germplasm of the invention may be combined with a canola germplasm that is characterized by a yellow seed coat to produce a germplasm that is able to deliver enhanced canola meal with desired characteristics imparted by each of the germplasms.

The foregoing and other features will become more apparent from the following detailed description of several embodiments, which proceeds with reference to the accompanying figures.

BRIEF DESCRIPTION OF THE FIGURES

FIG. 1 includes images of several canola varieties having dark seed coat color.

FIG. 2 includes data from seed composition analysis of certain *B. napus* inbred lines and hybrids. The seed samples were from replicated trials across Western Canada. Seed compositional data was predicted based on NIR, and subsequently verified using reference chemistry methods.

DETAILED DESCRIPTION OF THE INVENTION

I. Overview of Several Embodiments

Canola meal is the fraction of canola seed left after the oil extraction process. Canola meal is a source of protein, and therefore is utilized in several applications, including animal feed formulation and isolation of high value protein concentrates and isolates. Fiber within the seed coat, cotyledons and embryo that ends up in the meal limits inclusion rates of canola meal in monogastric animal species, and thus canola meals typically do not provide the same nutritional value as meals prepared from other sources (e.g., soybean). Yellow-seeded forms in species closely related to *B. napus* (e.g., *B. rapa* and *B. juncea*) have been shown to have lower levels of fiber in their seed and subsequent meal. This observation has motivated attempts to introduce low seed fiber trait into *B. napus* in a yellow seed color-dependent manner. The development of resulting yellow-seeded *B. napus* germplasm has demonstrated that fiber can be reduced in *B. napus* through this approach.

Prior to this invention, it was not thought that dark-seeded canola varieties would exhibit seed fiber content that was as low as has been observed in yellow-seeded varieties. Furthermore, dark-seeded canola lines containing reduced levels of anti-nutritional factors (e.g., fiber and polyphenolic compounds), and increased protein and phosphorous levels that would represent sources for improved canola meal have not been described. In some embodiments, canola genuplasms described herein provide combinations of several key enhanced meal composition attributes that are expressed independent of seed coat color. In particular embodiments, canola meals prepared from canola seeds comprising a germplasm of the invention may achieve higher dietary inclusion rates, for example, in swine and poultry diets.

Germplasms of the invention may be used (e.g., via selective breeding) to develop canola having desired seed component traits with one or more further desired traits (e.g., improved oil composition, increased oil production, modified protein composition, increased protein content, disease, parasite resistance, herbicide resistance, etc.). Germplasms of the invention may be used as a starting germplasm upon which additional changes in seed composition may be introduced, such that canola lines and hybrids may be developed that provide canola meals having increased improvements of the type described herein.

II. Abbreviations

ADF acid detergent fiber
ADL acid detergent lignin
AID Apparent ileal digestibility
AME apparent metabolizable energy
BSC black-seeded canola
CP crude protein percentage
DM dry matter concentration
ECM enhanced canola meal of the present invention
FAME fatty acid/fatty acid methyl esters
GE gross energy
HT "High Temperature" processing
LT "Low Temperature" processing
NDF neutral detergent fiber
NMR nuclear magnetic resonance
NIR near-infrared spectroscopy
SAE sinapic acid ester
SBM soybean meal
SER soluble extracted residue
SID standardized ileal digestibility
TAAA true amino acid availability
TDF total dietary fiber
TME true metabolizable energy
WF white flake III. Terms Backcrossing: Backcrossing methods may be used to introduce a nucleic acid sequence into plants. The backcrossing technique has been widely used for decades to introduce new traits into plants. Jensen, N., Ed. *Plant Breeding Methodology*, John Wiley & Sons, Inc., 1988. In a typical backcross protocol, the original variety of interest (recurrent parent) is crossed to a second variety (nonrecurrent parent) that carries a gene of interest to be transferred. The resulting progeny from this cross are then crossed again to the recurrent parent, and the process is repeated until a plant is obtained wherein essentially all of the desired morphological and physiological characteristics of the recurrent plant are recovered in the converted plant, in addition to the transferred gene from the nonrecurrent parent.

Canola oil: Canola oil refers to oil extracted from commercial varieties of rapeseed. To produce canola oil, seed is typically graded and blended at grain elevators to produce an acceptably uniform product. The blended seed is then crushed, and the oil is typically extracted with hexane and subsequently refined. The resulting oil may then be sold for use. Oil content is typically measured as a percentage of the whole dried seed, and particular oil contents are characteristic of different varieties of canola. Oil content can be readily and routinely determined using various analytical techniques, for example and without limitation: NMR; NIR; Soxhlet extraction, or by other methods widely available to those skilled in the art. See Bailey, *Industrial Oil & Fat Products* (1996), 5th Ed. Wiley Interscience Publication, New York, N.Y. The percent composition of total fatty acids is typically determined by extracting a sample of oil from seed, producing methyl esters of fatty acids present in the oil sample, and analyzing the proportions of the various fatty acids in the sample using gas chromatography. The fatty acid composition may also be a distinguishing characteristic of particular varieties.

Commercially useful: As used herein, the term "commercially useful" refers to plant lines and hybrids that have sufficient plant vigor and fertility, such that a crop of the plant line or hybrid can be produced by farmers using conventional farming equipment. In particular embodiments, plant commodity products with described components and/or qualities may be extracted from plants or plant materials of the commercially useful variety. For example, oil comprising desired oil components may be extracted from the seed of a commercially useful plant line or hybrid utilizing conventional crushing and extraction equipment. In certain embodiments, a commercially useful plant line is an inbred line or a hybrid line. "Agronomically elite" lines and hybrids typically have desirable agronomic characteristics; for example and without limitation: improved yield of at least one plant commodity product; maturity; disease resistance; and standability.

Elite line: Any plant line that has resulted from breeding and selection for superior agronomic performance. An elite plant is any plant from an elite line.

Enhanced canola meal: As used herein, the term "enhanced canola meal" means a canola meal with an enhanced composition derived from processing of canola seeds which have increased levels of protein and reduced levels of at least some antinutritional component. The enhanced canola meal which of the present invention may variously be referred to herein as "ECM," "black seeded canola ECM," "BSC ECM," or "DAS BSC ECM." However, the present invention is not intended to be limited to only ECM germplasm of black-seeded canola.

Essentially derived: In some embodiments, manipulations of plants, seeds, or parts thereof may lead to the creation of essentially derived varieties. As used herein, the term "essentially derived" follows the convention set forth by The International Union for the Protection of New Varieties of Plants (UPOV):

[A] variety shall be deemed to be essentially derived from another variety ("the initial variety") when
  (i) it is predominantly derived from the initial variety, or from a variety that is itself predominantly derived from the initial variety, while retaining the expression of the essential characteristics that result from the genotype or combination of genotypes of the initial variety;
  (ii) it is clearly distinguishable from the initial variety; and
  (iii) except for the differences which result from the act of derivation, it conforms to the initial variety in the expression of the essential characteristics that result from the genotype or combination of genotypes of the initial variety.

UPOV, *Sixth Meeting with International Organizations, Geneva*, Oct. 30, 1992 (*document prepared by the Office of the Union*).

Plant commodity product: As used herein, the term "plant commodity product" refers to commodities produced from a particular plant or plant part (e.g., a plant comprising a germplasm of the invention, and a plant part obtained from a plant comprising a germplasm of the invention). A commodity product may be, for example and without limitation: grain; meal; forage; protein; isolated protein; flour; oil; crushed or whole grains or seeds; any food product comprising any meal, oil, or crushed or whole grain; or silage.

Plant line: As used herein, a "line" refers to a group of plants that display little genetic variation (e.g., no genetic variation) between individuals for at least one trait. Inbred lines may be created by several generations of self-pollination and selection or, alternatively, by vegetative propagation from a single parent using tissue or cell culture techniques. As used herein, the terms "cultivar," "variety," and "type" are synonymous, and these terms refer to a line that is used for commercial production.

Plant material: As used herein, the term "plant material" refers to any processed or unprocessed material derived, in whole or in part, from a plant. For example and without limitation, a plant material may be a plant part, a seed, a fruit, a leaf, a root, a plant tissue, a plant tissue culture, a plant explant, or a plant cell.

Stability: As used herein, the term "stability," or "stable," refers to a given plant component or trait that is heritable and is maintained at substantially the same level through multiple seed generations. For example, a stable component may be maintained for at least three generations at substantially the same level. In this context, the term "substantially the same" may refer in some embodiments to a component maintained to within 25% between two different generations; within 20%; within 15%; within 10%; within 5%; within 3%; within 2%; and/or within 1%, as well as a component that is maintained perfectly between two different generations. In some embodiments, a stable plant component may be, for example and without limitation, an oil component; a protein component; a fiber component; a pigment component; a glucosinolate component; and a lignin component. The stability of a component may be affected by one or more environment factors. For example, the stability of an oil component may be affected by, for example and without limitation: temperature; location; stress; and the time of planting. Subsequent generations of a plant having a stable component under field conditions will be expected to produce the plant component in a similar manner, for example, as set forth above.

Trait or phenotype: The terms "trait" and "phenotype" are used interchangeably herein.

Variety or cultivar: The terms "variety" or "cultivar" refer herein to a plant line that is used for commercial production which is distinct, stable and uniform in its characteristics when propagated. In the case of a hybrid variety or cultivar, the parental lines are distinct, stable, and uniform in their characteristics.

Unless indicated otherwise, the terms "a" and "an" as used herein refer to at least one.

IV. Canola Germplasm Providing Desirable Seed Component Traits in a Seed Color-Independent Manner In a preferred embodiment, the invention provides a *Brassica* germplasm that may be used to obtain canola plants having desirable seed component traits in a seed color-independent manner. Particular exemplary canola inbred lines and hybrids comprising this germplasm are also provided.

Canola oil has generally been recognized as a very healthful oil, both for human and animal consumption. However, the meal component of the canola seed, which is left over after extracting the oil component, is inferior to soybean meal, because of its high fiber content and decreased nutritional value. In some embodiments, canola plants comprising a germplasm of the invention may mitigate or overcome these deficiencies, and may provide canola meals as a highly nutritious and economical source of animal feed. Canola meal is a by-product of canola oil production, and thus canola meals provided by this invention save valuable resources by allowing this by-product to be used competitively with other meals.

It was previously thought that yellow canola seed color per se was significant, because it was thought to correspond to improved nutritional characteristics of the meal component obtained after extraction of the oil. Some embodiments may provide, for the first time, a germplasm for dark-seeded (e.g., dark-, black-, and mottled-seeded), low-fiber canola that also provides a superior, high oleic and low linolenic oil, which germplasm also provides canola meal with improved nutritional characteristics (e.g., improved seed components). In some embodiments, a plant comprising a germplasm of the invention may surprisingly further provide these traits in combination with other valuable traits (for example and without limitation, excellent yield, high protein content, high oil content, and high oil quality). Dark-coated seeds in particular embodiments may have a considerably thinner seed coat than seeds produced by standard dark-seeded canola varieties. The thinner seed coat may result in a reduced fiber content in the meal, and an increase in seed oil and protein content, as compared to the levels of oil and protein in a standard dark-seeded variety. Dark-seeds produced by plants comprising a germplasm of the invention may therefore have higher oil and protein concentrations in their seeds than that observed in seeds produced by a standard dark-seeded canola plant.

In embodiments, a plant comprising a germplasm of the invention does not exhibit substantial agronomic and/or seed limitations. For example, such a plant may exhibit agronomic and/or seed qualities (e.g., germination; early season vigor; effect of seed treatments; seed harvesting and storability) that are at least as favorable as those exhibited by standard canola varieties. In particular embodiments, a plant comprising a germplasm of the invention may also comprise one or more further favorable traits exhibited by a pre-existing canola inbred line, for example and without limitation, a favorable fatty acid profile.

In embodiments, a plant comprising a germplasm of the invention may produce seeds comprising at least one of several nutritional characteristics. In particular embodiments, a seed produced by such a canola plant may comprise at least one nutritional characteristic selected from the group consisting of: favorable oil profile; high protein content; low fiber content (e.g., ADF and NDF (including low polyphenolic content)); (low fiber and high protein confer higher metabolizable energy); high phosphorous content; and low sinapic acid ester (SAE) content. In certain embodiments, "high" or "low" component content refers to a comparison between a seed produced by a reference plant comprising a germplasm of the invention and a seed produced by standard canola varieties. Thus, a plant producing a seed with "low" fiber content may produce a seed with a lower fiber content than is observed in a seed produced by standard canola varieties. And, a plant producing a seed with "high" protein content may produce a seed with a higher protein content than is observed in a seed produced by standard canola varieties.

In some embodiments, a substantially uniform assemblage of a rapeseed produced by a canola plant comprising at least one nutritional characteristic selected from the aforementioned group can be produced. Such seed can be used to produce a substantially uniform field of rape plants. Particular embodiments provide canola seeds comprising identifying combinations of the aforementioned characteristics. For example, the combined total oil and protein content of a seed may be a useful measure and unique characteristic of the seed.

Some embodiments provide a canola (e.g., a dark-seeded canola) comprising a germplasm of the invention that is capable of yielding canola oil having a NATREON-type oil profile. A "NATREON-type" or "NATREON-like" oil profile may signify an oleic acid content in a range of, for example, 68-80%; 70-78%; 71-77%; and 72-75%, with an alpha linolenic content below, for example, 3%. In particular embodiments, a seed obtained from a canola plant comprising a germplasm of the invention may yield oil having over 70%, over 71%, over 71.5%, and/or over 72% (e.g., 72.4% or 72.7%) oleic acid, while having a linolenic acid content of less than 2.4%, less than 2%, less than 1.9%, and/or less than 1.8% (e.g., 1.7%). In further embodiments, however, a canola comprising a germplasm of the invention may yield oils having, for example, an oleic acid content greater than 80%. In certain embodiments, a canola oil produced from a canola comprising a germplasm of the invention may be naturally stable (e.g., not artificially hydrogenated). The fatty acid content of canola oil may be readily and routinely determined according to known methods.

Thus, some embodiments provide a canola seed (e.g., a dark canola seed) comprising an oil fraction and a meal fraction, wherein the oil fraction may have an α-linolenic acid content of, for example, 3% or less (relative to the total fatty acid content of the seed), and an oleic acid content of, for example, 68% or more (relative to the total fatty acid content of the seed). By definition, the erucic acid (C22:1) content of such a seed may also be less than 2% by weight (compared to the total fatty acid content of the seed). In particular examples, the oil content of a canola seed may comprise 48%-50% of the seed by weight.

Fiber is a component of plant cell walls, and includes carbohydrate polymers (e.g., cellulose (linear glucose polymeric chains)); hemicellulose (branched chains of heteropolymers of, for example, galactose, xylose, arabinose, rhamnose, with phenolic molecules attached); and pectins (water soluble polymers of galacturonic acid, xylose, arabinose, with different degrees of methylation). Fiber also includes polyphenolic polymers (e.g., lignin-like polymers and condensed tannins). In theory, ADF fiber consists of cellulose and lignin. Condensed tannins are typically included in an ADF fraction, but condensed tannin content varies independently of ADF. In contrast, TDF is meal from which protein, solubles, and starch have been removed, and is composed of insoluble cell wall components (e.g., cellulose, hemicellulose, polyphenolics, and lignin).

In particular embodiments, a seed of a canola plant (e.g., a dark-seeded canola plant) comprising a germplasm of the invention may have a decreased ADF, as compared to a canola variety. In particular examples, the fiber content of the canola meal (whole seed, oil removed, on a dry matter basis) may comprise, for example and without limitation:

less than about 18% ADF (e.g., about 18% ADF, about 17% ADF about 16% ADF, about 15% ADF, about 14% ADF, about 13% ADF, about 12% ADF, about 11% ADF, and about 10% ADF and/or less than about 22% NDF (e.g., about 22.0% NDF, about 21% NDF, about 20% NDF, about 19% NDF, about 18% NDF, and about 17% NDF).

In particular embodiments, a seed of a canola plant comprising a germplasm of the invention may have increased protein content, as compared to a standard dark-seeded canola variety. In particular examples, the protein content the canola meal (whole seed, oil removed, on a dry matter basis) may comprise, for example and without limitation, greater than about 45% (e.g., about 45%, about 46%, about 47%, about 48%, about 49%, about 50%, about 51%, about 52%, about 53%, about 54%, about 55%, about 56%, about 57%, and about 58%) crude protein. Different canola varieties are characterized by particular protein contents. Protein content (% Nitrogen×6.25) may be determined using various well-known and routine analytical techniques, for example, NIR and Kjeldahl.

Phosphorous content may also be used to define seeds, plants, and lines of canola varieties in some embodiments. Such canola varieties may produce canola meal (whole seed, oil removed, on a dry matter basis) that has increased phosphorous content when compared to meal produced from standard canola varieties. For example, canola meal of the invention may comprise a phosphorous content of more than 1.2%; more than 1.3%; more than 1.4%; more than 1.5%; more than 1.6%, more than 1.7%, and/or more than 1.8%.

Various combinations of the aforementioned traits may also be identified in, and are exemplified by, the inbred canola lines and hybrids provided in the several Examples. These lines illustrate that germplasm of the invention can be used to provide and obtain various new combinations of a wide variety of advantageous canola characteristics and/or traits. For example, an inbred canola line comprising a germplasm of the invention may be crossed with another canola line that comprises a desired characteristic and/or trait to introduce desirable seed component characteristics of the inbred canola line comprising a germplasm of the invention. Calculations of seed components (e.g., fiber content, glucosinolate content, oil content, etc.) and other plant traits may be obtained using techniques that are known in the art and accepted in the industry. By selecting and propagating progeny plants from the cross that comprise the desired characteristics and/or traits of the parent varieties, new varieties may be created that comprise the desired combination of characteristics and/or traits.

V. Canola Meals Having Improved Nutritional Characteristics

Some embodiments provide meals comprising canola seed, wherein the canola seed has oil and meal characteristics as discussed above. For example, some embodiments include a hexane-extracted, air-dried canola meal (White Flake, or WF) comprising a novel combination of characteristics (e.g., seed components) as discussed above. Particular embodiments include meal comprising canola seed produced from a plant comprising a germplasm of the invention, and meal comprising seeds of progeny of a plant comprising a germplasm of the invention.

Canola inbred lines and hybrids comprising germplasm of the invention may in some embodiments deliver nutritionally-enhanced meal properties when utilized directly as a feed or food ingredient, and/or when utilized as feed stock for processing protein isolates and concentrates. For example, such canola inbred lines and hybrids may deliver animal feed performance superior to standard canola meal. In some embodiments, canola meal components (and animal feeds comprising them) may be utilized to provide good nutrition for a monogastric animal (e.g., swine and poultry).

In some embodiments, canola meal components (and animal feeds comprising them) may further be utilized to provide good nutrition for a ruminant animal (e.g., bovine animals, sheep, goats, and other animals of the suborder *Ruminantia*). The feeding of ruminants presents special problems and special opportunities. Special opportunities arise from the ability of ruminants to utilize insoluble cellulosic fiber, which may be broken down by certain microorganisms in the rumen of these animals, but is generally not digestible by monogastric mammals such as pigs. The special problems arise from the tendency of certain feeds to inhibit digestion of fiber in the rumen, and from the tendency of the rumen to limit the utilization of some of the components of certain feeds, such as fat and protein.

Oil-extracted *Brassica* seeds are a potential source of high-quality protein to be used in animal feed. After oil extraction, commodity canola meal comprises about 37% protein, compared to about 44-48% in soybean meal, which is currently widely preferred for feed and food purposes. Proteins contained in canola are rich in methionine and contain adequate quantities of lysine, both of which are limiting amino acids in most cereal and oilseed proteins. However, the use of canola meal as a protein source has been somewhat limited in certain animal feeds, as it contains unwanted constituents such as fiber, glucosinolates, and phenolics.

One nutritional aspect of rapeseed, from which canola was derived, is its high (30-55 µmol/g) level of glucosinolates, a sulfur-based compound. When canola foliage or seed is crushed, isothiocyanate esters are produced by the action of myrosinase on glucosinolates. These products inhibit synthesis of thyroxine by the thyroid and have other antimetabolic effects. Paul et al. (1986) Theor. Appl. Genet. 72:706-9. Thus, for human food use, the glucosinolate content of, for example, proteins derived from rapeseed meal should be reduced or eliminated to provide product safety.

An improved canola seed with, for example, favorable oil profile and content and low glucosinolate content in the seed would significantly reduce the need for hydrogenation. For example, the higher oleic acid and lower α-linolenic acid content of such oil may impart increased oxidative stability, thereby reducing the requirement for hydrogenation and the production of trans fatty acids. The reduction of seed glucosinolates would significantly reduce residual sulfur content in the oil. Sulfur poisons the nickel catalyst commonly used for hydrogenation. Koseoglu et al., Chapter 8, in *Canola and Rapeseed: Production, Chemistry, Nutrition, and Processing Technology*, Ed. Shahidi, Van Nostrand Reinhold, N.Y., 1990, pp. 123-48. Additionally, oil from a canola variety with low seed glucosinolates would be less expensive to hydrogenate.

Phenolic compounds in canola meal impart a bitter flavor, and are thought to be necessarily associated with a dark color in final protein products. Seed hulls, which are present in large amounts in standard canola meals, are indigestible for humans and other monogastric animals, and also provide an unsightly heterogeneous product.

The meal component of a seed produced by a canola plant comprising a germplasm of the invention may have, for example and without limitation: high protein; low fiber; higher phosphorous; and/or low SAEs. Insoluble fiber and polyphenolics, are anti-nutritional and impair protein and amino acid digestion. Thus, canola meals and animal feeds comprising canola meals having at least one seed component characteristic selected from the group consisting of reduced fiber content, increased protein content, reduced polyphenolic content, and increased phosphorous content, may be desirable in some applications.

In particular examples, a canola meal (oil-free, dry matter basis) may comprise a protein content of at least about 45% (e.g., about 45%, about 46%, about 47%, about 48%, about 49%, about 50%, about 51%, about 52%, about 53%, about 54%, about 55%, about 56%, about 57%, and about 58%).

Canola varieties comprising a germplasm of the invention may have good yields and produce seeds having much lower acid detergent fiber (ADF), compared to a reference canola line. Any empirical values determined for a component of a seed produced by a plant variety comprising a germplasm of the invention may be used in some embodiments to define plants, seeds, and oil of the plant variety. In some such examples, particular numbers may be used as endpoints to define ranges above, below, or in between any of the determined values. Exemplary ranges for oil characteristics and other seed components have been set forth above. Lines and seeds of plants thereof may also be defined by combinations of such ranges. For example, the oil characteristics discussed above together with characteristic fiber levels, polyphenolic levels, glucosinolate levels, protein levels, and phosphorous levels, for example, may be used to define particular lines and seeds thereof.

Not all of the aforementioned characteristics (e.g., seed component characteristics) are needed to define lines and seeds of some embodiments, but additional characteristics may be used to define such lines and seeds (for example and without limitation, metabolizable energy, digestible energy, biological energy, and net energy).

VI. Plants Comprising a Germplasm Conferring Desirable Seed Component Traits in a Seed Color-Independent Manner Desirable traits of particular canola inbred lines and hybrids comprising a germplasm of the invention may be transferred to other types of *Brassica* (through conventional breeding and the like), for example, *B. rapa*, and *B. juncea*, with the resulting plants producing seeds with desired characteristics (e.g., seed component characteristics) expressed independently of seed color. Thus, a *Brassica* variety into which one or more desirable traits of a particular canola inbred line or hybrid comprising a germplasm of the invention has been transferred may produce seeds with desired characteristics that are yellow-seeded or dark-seeded. Meals and seeds of such new or modified *Brassica* varieties may have a decreased level of seed fiber, increased protein level an increased level of phosphorous, and/or a decreased level of polyphenolics.

Some embodiments include not only yellow and dark seeds of canola comprising a germplasm as described and exemplified herein, but also plants grown or otherwise produced from such seeds, and tissue cultures of regenerable cells of the subject canola plants. Exemplified lines and hybrids were obtained without genetic engineering and without mutagenesis, thereby demonstrating the utility of the germplasm in producing new and modified canola varieties.

In some specific embodiments, specific exemplary canola inbred lines and hybrids are provided. As part of this disclosure, at least 2500 seeds of each of CL065620, CL044864, CL121460H, CL166102H and CL121466H have been deposited and made available to the public, subject to patent rights, but otherwise without restriction (except those restrictions expressly permitted by 37 C.F.R. §1.808(b)), with the American Type Culture Collection (ATCC), Rockville, Md. 20852. The deposits have been designated as ATCC Deposit Nos. PTA-11697, PTA-11696, PTA-11698, PTA-12570, and PTA-11699, respectively, with a deposit date of Feb. 22, 2011 for PTA11696 through PTA11699 and Feb. 21, 2012 for PTA-12570. The deposits will be maintained as set forth above at the ATCC depository, which is a public depository, for a period of 30 years, or five years after the most recent request, or for the effective life of the patent, whichever is longer, and a deposit will be replaced if it becomes nonviable during that period.

Some embodiments include a seed of any of the *Brassica napus* varieties disclosed herein. Some embodiments also include *Brassica napus* plants produced by such seed, as well as tissue cultures of regenerable cells of such plants. Also included is a *Brassica napus* plant regenerated from such tissue culture. In particular embodiments, such a plant may be capable of expressing all the morphological and physiological properties of an exemplified variety. *Brassica napus* plants of the particular embodiments may have identifying physiological and/or morphological characteristics of a plant grown from the deposited seed.

Also provided are processes of making crosses using a germplasm of the invention (e.g., as is found in exemplary canola inbred lines and hybrids provided herein) in at least one parent of the progeny of the above-described seeds. For example, some embodiments include an $F_1$ hybrid *B. napus* plant having as one or both parents any of the plants exemplified herein. Further embodiments include a *B. napus* seed produced by such an $F_1$ hybrid. In particular embodiments, a method for producing an $F_1$ hybrid *B. napus* seed comprises crossing an exemplified plant with a different inbred parent canola plant, and harvesting the resultant hybrid seed. Canola plants of the invention (e.g., a parent canola plant, and a canola plant produced by such a method for producing an $F_1$ hybrid) may be either a female or a male plant.

Characteristics of canola plants in some embodiments (e.g., oil and protein levels and/or profiles) may be further modified and/or improved by crossing a plant of the invention with another line having a modified characteristic (e.g., high oil and protein levels). Likewise, other characteristics may be improved by careful consideration of the parent plant. Canola lines comprising a germplasm of the invention may be beneficial for crossing their desirable seed component characteristics into other rape or canola lines in a seed color-independent manner. The germplasms of the invention allow these traits to be transferred into other plants within the same species by conventional plant breeding techniques, including cross-pollination and selection of progeny. In some embodiments, the desired traits can be transferred between species using conventional plant breeding techniques involving pollen transfer and selection. See, e.g., *Brassica crops and wild allies biology and breeding*, Eds. Tsunada et al., Japan Scientific Press, Tokyo (1980); *Physiological Potentials for Yield Improvement of Annual Oil and Protein Crops*, Eds. Diepenbrock and Becker, Blackwell Wissenschafts-Verlag Berlin, Vienna (1995); *Canola and Rapeseed*, Ed. Shahidi, Van Nostrand Reinhold, N.Y. (1990); and *Breeding Oilseed Brassicas*, Eds. Labana et al., Narosa Publishing House, New Dehli (1993).

In some embodiments, a method for transferring at least one desirable seed component characteristic in a seed color-independent manner comprises following the interspecific cross, self-pollinating members of the $F_1$ generation to produce $F_2$ seed. Backcrossing may then be conducted to obtain lines exhibiting the desired seed component characteristic(s). Additionally, protoplast fusion and nuclear transplant methods may be used to transfer a trait from one species to another. See, e.g., Ruesink, "Fusion of Higher Plant Protoplasts," *Methods in Enzymology*, Vol. LVIII, Eds. Jakoby and Pastan, Academic Press, Inc., New York, N.Y. (1979), and the references cited therein; and Carlson et al. (1972) Proc. Natl. Acad. Sci. USA 69:2292.

Having obtained and produced exemplary canola lines comprising a germplasm of the invention, a dark seed coat color may now be readily transferred with desirable seed component characteristics into other *Brassica* species, by conventional plant breeding techniques as set forth above. For example, a dark seed coat color may now be readily transferred with desirable seed component characteristics into commercially-available *B. rapa* varieties, for example and without limitation, Tobin, Horizon, and Colt. It is understood that the dark seed color does not have to be transferred along with other characteristics of the seed.

Given one of the exemplary varieties as a starting point, particular benefits afforded by the variety may be manipulated in a number of ways by the skilled practitioner without departing from the scope of the present invention. For example, the seed oil profile present in an exemplary variety may be transferred into other agronomically desirable *B. napus* variety by conventional plant breeding techniques involving cross-pollination and selection of the progeny, for example, wherein the germplasm of the exemplary variety is incorporated into the other agronomically desirable variety.

Particular embodiments may include exemplary varieties of *B. napus*, as well as essentially derived varieties that have been essentially derived from at least one of the exemplified varieties. In addition, embodiments of the invention may include a plant of at least one of the exemplified varieties, a plant of such an essentially derived variety, and/or a rape plant regenerated from plants or tissue (including pollen, seeds, and cells) produced therefrom.

Plant materials may be selected that are capable of regeneration, for example, seeds, microspores, ovules, pollen, vegetative parts, and microspores. In general, such plant cells may be selected from any variety of *Brassica*, including those having desired agronomic traits.

Regeneration techniques are known in the art. One can initially select cells capable of regeneration (e.g., seeds, microspores, ovules, pollen, and vegetative parts) from a selected plant or variety. These cells can optionally be subjected to mutagenesis. A plant may then be developed from the cells using regeneration, fertilization, and/or growing techniques based on the type of cells (and whether they are mutagenized). Manipulations of plants or seeds, or parts thereof, may lead to the creation of essentially derived varieties.

In some embodiments, desired seed component characteristics exhibited by plants comprising a germplasm of the invention may be introduced into a plant comprising a plurality of additional desirable traits in a seed color-independent manner, in order to produce a plant with both the desired seed component characteristics and the plurality of desirable traits. The process of introducing the desired seed component characteristics into a plant comprising one or more desirable traits in a seed color-independent manner is referred to as "stacking" of these traits. In some examples, stacking of the desired seed component characteristics with a plurality of desirable traits may result in further improvements in seed component characteristics. In some examples, stacking of the desired seed component characteristics with a plurality of desirable traits may result in a canola plant having the desired seed component characteristics in addition to one or more (e.g., all) of the plurality of desirable traits.

Examples of traits that may be desirable for combination with desired seed component characteristics include, for example and without limitation: plant disease resistance genes (See, e.g., Jones et al. (1994) Science 266:789 (tomato Cf-9 gene for resistance to *Cladosporium fulvum*); Martin et al. (1993) Science 262:1432 (tomato Pto gene for resistance to *Pseudomonas syringae*); and Mindrinos et al. (1994) Cell 78:1089 (RSP2 gene for resistance to *Pseudomonas syringae*)); a gene conferring resistance to a pest; a *Bacillus thuringiensis* protein, a derivative thereof, or a synthetic polypeptide modeled thereon (See, e.g., Geiser et al. (1986) Gene 48:109 (Bt δ-endotoxin gene; DNA molecules encoding δ-endotoxin genes can be purchased from American Type Culture Collection (Manassas, Va.), for example, under ATCC Accession Nos. 40098; 67136; 31995; and 31998)); a lectin (See, for example, Van Damme et al. (1994) Plant Molec. Biol. 24:25 (*Clivia miniata* mannose-binding lectin genes)); a vitamin-binding protein, e.g., avidin (See International PCT Publication US93/06487 (use of avidin and avidin homologues as larvicides against insect pests)); an enzyme inhibitor; a protease or proteinase inhibitor (See, e.g., Abe et al. (1987) J. Biol. Chem. 262:16793 (rice cysteine proteinase inhibitor); Huub et al. (1993) Plant Molec. Biol. 21:985 (tobacco proteinase inhibitor I; and U.S. Pat. No. 5,494,813); an amylase inhibitor (See Sumitani et al. (1993) Biosci. Biotech. Biochem. 57:1243 (*Streptomyces nitrosporeus* alpha-amylase inhibitor)); an insect-specific hormone or pheromone, e.g., an ecdysteroid or juvenile hormone, a variant thereof, a mimetic based thereon, or an antagonist or agonist thereof (See, e.g., Hammock et al. (1990) Nature 344:458 (inactivator of juvenile hormone)); an insect-specific peptide or neuropeptide that disrupts the physiology of the affected pest (See, e.g., Regan (1994) J. Biol. Chem. 269:9 (insect diuretic hormone receptor); Pratt et al. (1989) Biochem. Biophys. Res. Comm. 163:1243 (allostatin from *Diploptera puntata*); U.S. Pat. No. 5,266,317 (insect-specific, paralytic neurotoxins)); an insect-specific venom produced in nature by a snake, a wasp, or other organism (See, e.g., Pang et al. (1992) Gene 116:165 (a scorpion insectotoxic peptide)); an enzyme responsible for a hyperaccumulation of a monoterpene, a sesquiterpene, a steroid, hydroxamic acid, a phenylpropanoid derivative or another non-protein molecule with insecticidal activity; an enzyme involved in the modification, including the post-translational modification, of a biologically active molecule, e.g., a glycolytic enzyme; a proteolytic enzyme; a lipolytic enzyme; a nuclease; a cyclase; a transaminase; an esterase; a hydrolase; a phosphatase; a kinase; a phosphorylase; a polymerase; an elastase; a chitinase; or a glucanase, whether natural or synthetic (See International PCT Publication WO 93/02197 (a callase gene); DNA molecules which contain chitinase-encoding sequences (for example, from the ATCC, under Accession Nos. 39637 and 67152); Kramer et al. (1993) Insect Biochem. Molec. Biol. 23:691 (tobacco hornworm chitinase); and Kawalleck et al. (1993) Plant Molec. Biol. 21:673 (parsley ubi4-2 polyubiquitin gene); a molecule that stimulates signal transduction (See, e.g., Botella et al. (1994) Plant Molec. Biol. 24:757 (calmodulin); and Griess et al. (1994) Plant Physiol. 104:1467 (maize calmodulin); a hydrophobic moment peptide (See, e.g., International PCT Publication WO 95/16776 (peptide derivatives of Tachyplesin which inhibit fungal plant pathogens); and International PCT Publication WO 95/18855 (synthetic antimicrobial peptides that confer disease resistance)); a membrane permease, a channel former, or a channel blocker (See, e.g., Jaynes et al. (1993) Plant Sci 89:43 (a cecropin-β lytic peptide analog to render transgenic plants resistant to *Pseudomonas solanacearum*); a viral-invasive protein or a complex toxin derived therefrom (See, e.g., Beachy et al. (1990) Ann. rev. Phytopathol. 28:451 (coat protein-mediated resistance against alfalfa mosaic virus, cucumber mosaic virus, tobacco streak virus, potato virus X, potato virus Y, tobacco etch virus, tobacco rattle virus and tobacco mosaic virus)); an insect-specific antibody or an immunotoxin derived therefrom (See, e.g., Taylor et al., Abstract #497, Seventh Int'l Symposium on Molecular Plant-Microbe Interactions (Edinburgh, Scotland) (1994) (enzymatic inactivation via production of single-chain antibody fragments); a virus-specific antibody (See, e.g., Tavladoraki et al. (1993) Nature 366:469 (recombinant antibody genes for protection from virus attack)); a developmental-arrestive protein produced in nature by a pathogen or a parasite (See, e.g., Lamb et al. (1992) Bio/Technology 10:1436 (fungal endo polygalacturonases facilitate fungal colonization and plant nutrient release by solubilizing plant cell wall homo-α-1,4-D-galacturonase; Toubart et al. (1992) Plant J. 2:367 (endopolygalacturonase-inhibiting protein)); and a developmental-arrestive protein produced in nature by a plant (See, e.g., Logemann et al. (1992) Bio/Technology 10:305 (barley ribosome-inactivating gene providing increased resistance to fungal disease)).

Further examples of traits that may be desirable for combination with desired seed component characteristics include, for example and without limitation: genes that confer resistance to a herbicide (Lee et al. (1988) EMBO J. 7:1241 (mutant ALS enzyme); Miki et al. (1990) Theor. Appl. Genet. 80:449 (mutant AHAS enzyme); U.S. Pat. Nos. 4,940,835 and 6,248,876 (mutant 5-enolpyruvylshikimate-3-phosphate synthase (EPSPs) genes providing glyphosate resistance); U.S. Pat. No. 4,769,061 and ATCC accession number 39256 (aroA genes); glyphosate acetyl transferase genes (glyphosate resistance); other phosphono compounds from *Streptomyces* species, including *Streptomyces hygroscopicus* and *Streptomyces viridichromogenes*) such as those described in European application No. 0 242 246 and DeGreef et al. (1989) Bio/Technology 7:61 (glufosinate phosphinothricin acetyl transferase (PAT) genes providing glyphosate resistance); pyridinoxy or phenoxy proprionic acids and cyclohexones (glyphosate resistance); European patent application No. 0 333 033 and U.S. Pat. No. 4,975, 374 (glutamine synthetase genes providing resistance to herbicides such as L-phosphinothricin); Marshall et al. (1992) Theor. Appl. Genet. 83:435 (Acc1-51, Acc1-S2, and Acc1-S3 genes providing resistance to phenoxy proprionic acids and cyclohexones, such as sethoxydim and haloxyfop); WO 2005012515 (GAT genes providing glyphosate resistance); WO 2005107437 (Genes conferring resistance to 2,4-D, fop and pyridyloxy auxin herbicides); and an herbicide that inhibits photosynthesis, such as a triazine (psbA and gs+ genes) or a benzonitrile (nitrilase gene) (See, e.g., Przibila et al. (1991) Plant Cell 3:169 (mutant psbA genes); nucleotide sequences for nitrilase genes are disclosed in U.S. Pat. No. 4,810,648, and DNA molecules containing these genes are available under ATCC Accession Nos. 53435, 67441, and 67442; and Hayes et al. (1992) Biochem. J. 285:173 (glutathione S-transferase)).

Further examples of traits that may be desirable for combination with desired seed component characteristics include, for example and without limitation, genes that confer or contribute to a value-added trait, for example, modified fatty acid metabolism (See, e.g., Knultzon et al. (1992) Proc. Natl. Acad. Sci. U.S.A. 89:2624 (an antisense gene of stearyl-ACP desaturase to increase stearic acid content of the plant)); decreased phytate content (See, e.g., Van Hartingsveldt et al. (1993) Gene 127:87 (an *Aspergillus niger* phytase gene enhances breakdown of phytate, adding more free phosphate to the transformed plant); and Raboy et al. (1990) Maydica 35:383 (cloning and reintroduction of DNA associated with an allele responsible for maize mutants having low levels of phytic acid)); and modified carbohydrate composition effected, for example, by transforming plants with a gene coding for an enzyme that alters the branching pattern of starch (See, e.g., Shiroza et al. (1988) J. Bacteol. 170:810 (Streptococcus mutant fructosyltransferase gene); Steinmetz et al. (1985) Mol. Gen. Genet. 20:220 (levansucrase gene); Pen et al. (1992) Bio/Technology 10:292 (α-amylase); Elliot et al. (1993) Plant Molec. Biol. 21:515 (tomato invertase genes); Sogaard et al. (1993) J. Biol. Chem. 268:22480 (barley α-amylase gene); and Fisher et al. (1993) Plant Physiol. 102:1045 (maize endosperm starch branching enzyme II)).

All references, including publications, patents, and patent applications, cited herein are hereby incorporated by reference to the extent they are not inconsistent with the explicit details of this disclosure, and are so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

The following Examples are provided to illustrate certain particular features and/or aspects of the claimed invention. These Examples should not be construed to limit the disclosure to the particular features or aspects described.

EXAMPLES

Example 1

Average Nutrient Composition and Value of Enhanced Canola Meal (EMC) and Conventional Canola Meal Several analytical and functional studies were conducted between 2009 and 2012 to assess the nutrient composition and value of ECM lines and hybrids of the present invention. Testing was conducted on whole unprocessed seed, partially processed meal and fully processed meal to account for possible processing effects on nutritional composition and value. Samples were analyzed at the Universities of Illinois, Missouri, Georgia and Manitoba. This compositional information was used to estimate the energy value of enhanced canola meal versus conventional canola meal using standard prediction equations. Biological evaluation of the samples for poultry energy and amino acid digestibility were done at the Universities of Illinois and Georgia. Biological evaluation of the samples for swine energy and amino acid digestibility was conducted at the University of Illinois. The summary nutrient composition differences between ECM lines (ranges or average) and conventional canola meal are shown in Table 1. Details of the relevant procedures and studies are outlined in succeeding examples.

TABLE 1

Average nutrient composition of ECM and conventional canola meal.

| Nutrient, as is (88% dry matter, 3% oil) | ECM | Conventional canola meal |
|---|---|---|
| Dry matter, % | 88 | 88 |
| Protein, % | 43-44 (44) | 37 |
| Fat, % | 3 | 3 |
| Ash, % | 7.2 | 6.7 |
| Phosphorus, % | 1.1-1.4 (1.3) | 1.0 |
| Digestible phosphorus, % | 0.43 | 0.33 |
| ADF, % | 12-15 (14) | 19 |
| Lignin/polyphenols, % | 3-5 (4) | 6 |
| Cellulose, % | 4-5 | 5-6 |
| NDF % | 17-22 | 25 |
| Sugars, % | 7 | 7 |
| Lysine, % | 2.46 | 2.07 |
| Lysine, % crude protein | 5.6 | 5.6 |
| Lysine poultry availability, TAAA % | 84 | 82 |
| Lysine swine digestibility, SID % | 76 | 72 |
| Poultry ME**, kcal/kg | 2200 | 2000 |
| Swine NE**, kcal/kg | 1800 | 1600 |

*Number in parenthesis is average
**Predicted from nutrient composition

The ECM lines show several distinct improvements in nutrient composition which provide value in animal feeding. As illustrated in Table 1, ECM is approximately 7% points higher in protein than conventional canola meal. Further, the balance of essential amino acids (as a percentage of protein) is maintained at the higher protein levels. The digestibility of the amino acids in ECM by poultry and swine is at least as good as in conventional canola meal, and the key amino acid lysine appears to have slightly higher digestibility. The ECM lines showed lower levels of fiber components that are found in cell walls and hull, specifically approximately 2% points lower levels of lignin/polyphenols, 1% point lower cellulose, 3% points lower ADF residue (3% points), and 5% points lower ADF levels.

The higher levels of protein and lower levels of fiber components correlate with an approximately 10% increased biological energy in the ECM lines. These lines also showed higher levels of phosphorus, which is an expensive nutrient to add to animal feeds. Table 1.

Example 2

POS White Flake (WF), LT and HT Meal Processes

ECM seed and conventional canola seed were processed at the POS Pilot Plant in Saskatoon, Calif. according to the following procedures:
Materials
Approximately 1.5 MT of the ECM test line (CL44864) canola seed was received at POS on Aug. 2, 2011. Approximately 3.0 MT of commodity control canola seed was received at POS on Aug. 3, 2011. Sources for major materials follow.
Hexane/iso-hexane: Univar, Saskatoon, SK.
Hyflo Super-cel Filter Aid: Manville Products Corp., Denver, Colo.
Nitrogen: Air Liquide, Saskatoon, SK.
Filter Cloth, monofilament: Porritts and Spensor, Pointe Claire, PQ.
Filter Paper, 55 lb tan style 1138-55: Porritts and Spensor, Pointe Claire, PQ.
Methods—Pilot Plant Processing Between each canola variety, all equipment in the "Primary" processing plant was vacuumed or swept clean. Inflammable, the extractor was not shutdown in between trials. However, the extractor chain, Schnecken and solvent recovery systems were kept running to empty the equipment between canola varieties. The vacuum was not shut down so all vapors were drawn to the condenser, condensed and discharged into the solvent work tank. This prevented water from condensing in the Schnecken and plugging the conveyor. Canola samples were pressed/extracted in the following order:
1. Control HT
2. Control LT
3. ECM test line (CL44864) LT Flaking Flaking is carried out to rupture oil cells and prepare a thin flake with a large surface area for cooking/prepressing by passing the seed through a set of smooth rollers. Flake thickness and moisture are adjusted to minimize the quantity of fines produced. High fines levels result in a press cake with poor solvent percolation properties.

The canola seed was flaked using the minimum roll gap setting. The flake thickness range for each lot was as follows:

| | |
|---|---|
| 1. Control HT | 0.21-0.23 mm |
| 2. Control LT | 0.19-0.23 mm |
| 3. ECM test line (CL44864) LT | 0.21-0.23 mm |

The feed rate was controlled by the rate of pressing and was approximately 133-150 kg/hr. Flaker: 14" dia×28" width Lauhoff Flakmaster Flaking Mill Model S-28, Serial No. 7801 manufactured by Lauhoff Corporation.
Cooking (Conditioning)

Cooking is done to further rupture oil cells, make flakes pliable and increase the efficiency of the expeller by lowering the viscosity of the oil contained. Cooking is also done to deactivate enzymes in the seed. The cooker was preheated prior to the start of each run. Steam pressures were adjusted while running to maintain the desired flake temperatures. Temperatures in the trays for the Control HT lot were as follows:

| | |
|---|---|
| Top tray | 60 ± 5° C. |
| Bottom tray | 97 ± 3° C. |

Temperatures in the trays for the Control LT lot plus ECM test line (CL44864) LT lot were as follows:

| | |
|---|---|
| Top tray | 60 ± 5° C. |
| Bottom tray | 93 ± 2° C. |

Cooker: Two tray Simon-Rosedown cookers were used. Each compartment was 36 cm high (21 cm working height) and 91 cm in diameter, and supplied with a sweeping arm for material agitation. Steam was used on the jacket for dry heat as well as direct steam can be added to the contents of the vessel. The cooker was mounted over the screw press for direct feeding.
Pressing Pressing removes approximately ⅔ of the oil and produces presscake suitable for solvent extraction. The presscake requires crush resistance to hold up in the extractor and porosity for good mass transfer and drainage. The flaked and cooked seed was pressed using a Simon-Rosedown pre-press.

The crude press oil was collected in a tank.

Pre-press: Simon-Rosedowns 9.5 cm diameter by 94 cm long screw press. An operational screw speed of 17 rpm was used.

Solvent Extraction and Desolventization

Solvent extraction is the contacting of press cake with hexane to remove the oil from the cake mass. Two mechanisms were in operation: leaching of the oil into the solvent, and the washing of the marc (hexane-solids) with progressively weaker miscellas (hexane-oil). Extraction is normally a continuous counter-current process.

The canola control HT press cake was iso-hexane/hexane extracted using a total residence time of approximately 90 minutes (loop in to loop out), a solvent to solid ratio of approximately 2.5:1 (w:w) and a miscella temperature of 52±5° C. (The canola press cake feed rate was approximately 90 kg/hr at the 90 minute retention time and solvent flow rate was 220±10 kg/hr.).

A sample of commodity canola white flake (WF) was removed before desolventization and air dried.

The crude oil was desolventized in a rising film evaporator and steam stripper. Desolventization of the marc (hexane-solids) was done in a steam-jacketed Schnecken screw and 2-tray desolventizer-toaster. Sparge steam was added to the top DT tray. The target temperatures in the trays were as follows:

| Schnecken Exit: | <60° C. |
|---|---|
| Desolventized Tray: | 102 ± 3° C. |
| Toasting Tray: | 102 ± 3° C. |

The canola control LT and ECM test line (CL44864) LT lot press cake was iso-hexane/hexane extracted using a total residence time of approximately 110 minutes (loop in to loop out), a solvent to solid ratio of approximately 2.5:1 (w:w) and a miscella temperature of 52±5° C. (The canola press cake feed rate was approximately 80 kg/hr at the 110 minute retention time and solvent flow rate was 220±10 kg/hr).

A sample of ECM test line white flake (WF) was removed prior to desolventization, and air dried.

The crude oil was desolventized in a rising film evaporator and steam stripper. Desolventization of the marc (hexane-solids) was done in a steam jacketed Schnecken screw and 2 tray desolventizer-toaster. Sparge steam was added to the top DT tray. The target temperatures in the trays were as follows:

| Schnecken Exit: | <60° C. |
|---|---|
| Desolventized Tray: | 93 ± 2° C. |
| Toasting Tray: | 93 ± 2° C. |

Extractor: All stainless Crown Iron Works Loop Extractor (Type II). The extraction bed was 20.3 cm wide×12.7 cm deep by 680 cm in length. In addition, the unit includes miscella desolventization using a rising film evaporator and steam stripper and marc (solids plus solvent) desolventization using a steam jacketed Schnecken screw and 2 tray desolventizer-toaster. The recovered solvent was collected and recycled.

Vacuum Drying

Vacuum drying was done to dry the defatted LT canola meal to <12% moisture.

The only defatted canola meal lot that required drying was the control LT lot. Approximately 225 kg of defatted meal was loaded into the Littleford Reactor Dryer. The meal was then heated to 75±2° C. under a vacuum of 10-15" HG. Sampling of the meal for moisture analysis began at ~60° C. and occurred every 15 minutes until the moisture was <12%. The meal was then discharged into a bulk sack. The above procedure was repeated until all of the meal was dried. Vacuum Dryer: 600 Liter Model FKM600-D (2Z) Littleford Reactor, serial #5132, Littleford Day, Florence, Ky.

Hammer Milling

Hammer milling was carried out to produce a uniform particle size.

The dried meal was hammer-milled using an 8/64" screen. The hammer mill was vacuum-cleaned between each lot of meal. The meal was packaged into fiber drums and stored at ambient temperature until shipping.

The order in which the canola meal was hammer milled was as follows:
1. Control HT.
2. ECM test line (CL44864) LT.
3. Control LT.

Hammer mill: Prater Industries, Model G5HFSI, serial #5075, Chicago, Ill.

Example 3

Indianapolis White Flake Process

Canola seed of the present invention may be processed to produce canola white flakes using the procedure originally described in Bailey's Industrial Oil & Fat Products (1996), 5th Ed., Chapter 2, Wiley Interscience Publication, New York, N.Y.

To extract oil from the canola seed, the canola seed is first flaked by coffee grinding and heat treated in an oven to 85° C.±10° C. for at least 20 minutes. After heat treatment, the ground seed is pressed using a Taby Press Type-20A Press (Täby Skeppsta, Örebro, Sweden). The resulting presscake from the Taby Press is solvent extracted to remove any remaining residual oil.

Presscake from the oilseed pressing step is then solvent extracted to remove and collect any remaining residual oil. The presscake is placed into stainless steel thimbles which are placed into a custom made Soxhlet™ extractor from LaSalle Glassware (Guelph, ON). Hexane may be used as the extraction solvent and the Soxhlet™ extractor system is allowed to operate for 9-10 hours. The solvent extracted presscake is then removed from the thimbles and spread across a tray to a cake thickness of less than one inch. The solvent extracted cake is allowed to air desolventize for 24 hours prior to milling. The desolventized white flake is then milled using, for example, a Robot Coupe R2N Ultra B (Jackson, Miss.).

Example 4

Sample Analysis

Chemical and nutrient analyses of ECM and conventional canola samples may variously be performed using the methods as outlined below. Canola meal samples were analyzed for dry matter (method 930.15; AOAC International. 2007. Official Methods. Of Analysis of AOAC Int. 18th ed. Rev. 2. W. Hortwitz and G. W. Latimer Jr., eds. Assoc. Off. Anal.

Chem. Int., Gaithersburg. Md. (hereinafter "AOAC Int., 2007")), ash (method 942.05; AOAC Int.), and GE via bomb colorimeter (Model 6300, Parr Instruments, Moline, Ill.). AOAC International (2007) Official Methods of Analysis of AOAC Int., 18th ed. Rev. 2, Hortwitz and Latimer, eds. Assoc. Off. Anal. Chem. Int., Gaithersburg. Md. Acid hydrolyzed ether extract (AEE) was determined by acid hydrolysis using 3N HCl (Sanderson) followed by crude fat extraction with petroleum ether (method 954.02; AOAC Int.) on a Soxtec 2050 automated analyzer (FOSS North America, Eden Prairie, Minn.). Sanderson (1986), "A new method of analysis of feeding stuffs for the determination of crude oils and fats," Pages 77-81, in *Recent Advances in Animal Nutrition*, Haresign and Cole, eds. Butterworths, London, U.K. Crude protein was measured by combustion (method 990.03; AOAC Int.) on an Elementar Rapid N-cube protein/nitrogen apparatus (Elementar Americas Inc., Mt. Laurel, N.J.); amino acids according to method 982.30 E (A, B, and C) [AOAC Int.]; crude fiber according to method 978.10 (AOAC Int.); ADF and lignin according to method 973.18 (AOAC Int.); and NDF according to Ho1st (Hoist, D. O. 1973. Hoist filtration apparatus for Van Soest detergent fiber analysis. J. AOAC. 56:1352-1356). The sugar profile (glucose, fructose, sucrose, lactose, maltose) followed Churms (Churms, 1982, Carbohydrates in Handbook of Chromatography. Zweig and Sherma, eds. CRC Press, Boca Raton, Fla.), and Kakehi and Honda (1989. Silyl ethers of carbohydrates. Page 43-85 in Analysis of Carbohydrates by GLC and MS. C. J. Biermann and G. D. McGinnis, eds. CRC Press, Boca Raton, Fla.). Oligosaccharides (raffinose, stachyose, verbascose) were analyzed according to Churms; minerals (Ca, P, Fe, Mg, Mn, Cu, Na, K, S, Mo, Zn, Se, Co, Cr) via Inductive Coupled Plasma-Optical Emission Spectroscopy (ICP-OES) [method 985.01 (A, B, and C); AOAC Int.], and phytate according to Ellis et al (1977. Quantitative determination of phytate in the presence of high inorganic phosphate. Anal. Biochem. 77:536-539.)

Example 5

Baseline Analytical Results on ECM Indianapolis White Flake Samples and Conventional Canola Meal Nutrient composition of pilot plant prepared toasted ECM and conventional canola meal. Several ECM lines (44864, 121460, 121466, and 65620) were processed at the Dow Agro Sciences laboratory in Indianapolis using a process similar to commercial canola meal processing but without the final step of desolventizer/toasting after solvent extraction of the oil from the seed. This process and the resulting samples are referred to as "Indianapolis white flake". The processing parameters are outlined in Example 3. These ECM Indianapolis white flake samples were tested at the Universities of Illinois and Missouri and the results are shown in Tables 2a, 2b, and 2c. The canola meal control is a commercially-prepared canola meal that was toasted. Values are expressed on a dry matter basis, but including oil.

TABLE 2a

Nutrient composition of ECM Indianapolis White Flake canola meal samples compared with conventional canola meal.

| Component, % DM, including oil | 44864 (2010) | 44864 (2011) | 121460 (2011) | 121466 (2011) | 65620 (2011) | Conventional Canola meal | ECM average | ECM − Canola meal |
|---|---|---|---|---|---|---|---|---|
| Crude protein | 49.4 | 49.4 | 50.3 | 50.1 | 49.5 | 43.0 | 49.7 | 6.7 |
| Fat | 3.1 | 2.6 | 3.2 | 3.4 | 3.1 | 4.3 | 3.1 | −1.2 |
| Ash | 8.4 | 8.3 | 7.7 | 8.3 | 7.8 | 7.4 | 8.1 | 0.7 |
| Simple sugars | 4.3 | 0.5 | 0.6 | 0.6 | 1.1 | 0 | 1.4 | 1.4 |
| Sucrose | 4.6 | 8.3 | 7.6 | 5.9 | 7.7 | 8.1 | 6.8 | −1.3 |
| Oligosaccharides | 0.5 | 3.0 | 4.0 | 3.4 | 2.8 | 2.8 | 2.7 | −0.1 |
| Starch | 0.1 | 0 | 0 | 0 | 0 | 0 | 0 | 0 |
| NDF | 20.7 | 19.5 | 20.3 | 21.2 | 20.0 | 33.0 | 20.3 | −12.7 |
| ADF | 15.3 | 14.6 | 15.6 | 16.4 | 14.6 | 19.0 | 15.3 | −3.7 |
| Lignin & polyphenols | 4.5 | 4.1 | 5.2 | 6.2 | 4.2 | 7.2 | 4.9 | −2.3 |

Analytical results on ECM Indianapolis white flake samples from the Universities of Illinois and Missouri were similar to the results on whole seed from the University of Manitoba. Oligosaccharides were lower and simple sugars were higher in sample 44864 (2010) than in the other ECM samples, including the 44864 grown in 2011. It appears that for the 2010 sample, the growing plant catabolized some sucrose and oligosaccharides to simple sugars near the time of harvest.

The higher protein, lower ADF and lower lignin & polyphenols seen in the ECM lines compared to conventional canola meal, using the Indianapolis white flake protocol, are similar to the results seen with whole seed. The value of 33% NDF for the commercial meal is at the higher end of the typical range.

TABLE 2b

Amino acid composition (% of crude protein) of ECM Indianapolis White Flake samples compared with conventional canola meal.

| Component, % DM, including oil, % of CP | 44864 (2010) | 44864 (2011) | 121460 (2011) | 121466 (2011) | 65620 (2011) | Conventional Canola meal | ECM avg | ECM − Conventional Canola meal |
|---|---|---|---|---|---|---|---|---|
| Crude protein | 49.4 | 49.4 | 50.3 | 50.1 | 49.5 | 43.0 | 49.7 | 6.7 |
| Essential amino acids | | | | | | | | |
| Arginine | 5.63 | 5.67 | 6.04 | 5.95 | 6.02 | 5.78 | 5.86 | 0.08 |
| Histidine | 2.53 | 2.60 | 2.55 | 2.52 | 2.64 | 2.68 | 2.57 | −0.11 |
| Isoleucine | 3.56 | 3.81 | 3.83 | 3.70 | 3.77 | 4.15 | 3.73 | −0.42 |
| Leucine | 6.50 | 6.50 | 6.91 | 6.76 | 6.84 | 7.01 | 6.70 | −0.31 |
| Lysine | 5.49 | 5.69 | 5.54 | 5.37 | 5.90 | 5.37 | 5.60 | 0.23* |
| Methionine | 1.80 | 1.87 | 1.89 | 1.81 | 1.94 | 1.99 | 1.86 | −0.13* |
| Phenylalanine | 3.76 | 3.68 | 3.93 | 3.87 | 3.91 | 3.98 | 3.83 | −0.15 |
| Threonine | 3.82 | 3.82 | 4.17 | 4.01 | 4.12 | 4.12 | 4.01 | −0.11* |
| Tryptophan | 1.27 | 1.23 | 1.29 | 1.35 | 1.19 | 1.23 | 1.27 | 0.04* |
| Valine | 4.66 | 4.78 | 4.87 | 4.71 | 4.80 | 5.21 | 4.76 | −0.45 |
| Non-essential aa | | | | | | | | |
| Alanine | 4.07 | 3.98 | 4.16 | 4.05 | 4.25 | 4.32 | 4.10 | −0.22 |
| Aspartic acid | 6.77 | 6.24 | 7.35 | 7.06 | 6.82 | 6.87 | 6.85 | −0.02 |
| Cystine | 2.35 | 2.47 | 2.26 | 2.20 | 2.53 | 2.30 | 2.36 | 0.06 |
| Glutamic acid | 16.57 | 17.19 | 16.92 | 16.54 | 17.54 | 16.84 | 16.95 | 0.11 |
| Glycine | 4.50 | 4.63 | 4.85 | 4.76 | 4.89 | 4.98 | 4.73 | −0.25 |
| Proline | 5.41 | 5.80 | 5.92 | 5.78 | 5.98 | 6.20 | 5.78 | −0.42 |
| Serine | 3.76 | 3.57 | 3.75 | 3.65 | 4.04 | 3.54 | 3.75 | 0.21 |
| Tyrosine | 2.66 | 2.47 | 2.73 | 2.70 | 2.77 | 2.83 | 2.67 | −0.16 |

*Regarded as the major limiting essential amino acids in poultry and swine feeds As was the case with whole seed, the results in Table 2b show that the amino acid composition (as a percentage of crude protein) is similar for both ECM Indianapolis white flake samples and commercial canola meal. This indicates that as protein has increased in the ECM lines, the important amino acids have increased proportionately.

The mineral content of the ECM Indianapolis white flake samples are similar to conventional canola meal with two exceptions: phosphorus and sodium. As was the case with the University of Manitoba results on whole seed, the phosphorus in the ECM lines does appear to be consistently higher than conventional canola meal. The extra sodium in TABLE 2c Mineral composition of Indianapolis ECM white flake samples compared with conventional canola meal.

| Component, DM basis, including oil | 44864 (2010) | 44864 (2011) | 121460 (2011) | 121466 (2011) | 65620 (2011) | Convent. Canola meal | ECM average | ECM − Convent, Canola meal |
|---|---|---|---|---|---|---|---|---|
| Calcium, % | 0.83 | 0.84 | 0.75 | 0.74 | 0.76 | 0.80 | 0.78 | −0.02 |
| Phosphorus, % | 1.50 | 1.49 | 1.39 | 1.50 | 1.42 | 1.14 | 1.46 | 0.32 |
| Phytic acid, % | 4.25 | 4.16 | 4.05 | 4.52 | 3.81 | 2.96 | 4.16 | 1.20 |
| Sodium, % | 0.001 | 0.003 | 0.003 | 0.002 | 0.002 | 0.13 | 0.002 | −0.13 |
| Potassium, % | 1.65 | 1.67 | 1.36 | 1.43 | 1.45 | 1.32 | 1.51 | 0.19 |
| Sulfur, % | — | 0.97 | 0.87 | 0.85 | 0.87 | 0.83 | 0.89 | 0.06 |
| Magnesium, % | 0.67 | 0.69 | 0.64 | 0.62 | 0.68 | 0.62 | 0.66 | 0.04 |
| Iron, mg/kg | 94 | 124 | 93 | 88 | 98 | 150 | 99 | −51 |
| Manganese, mg/kg | 56 | 83 | 98 | 85 | 77 | 64 | 80 | 16 |
| Cobalt, mg/kg | 0.3 | 0.1 | 0.1 | 2.7 | 3.2 | 1.3 | 1.3 | 0 |
| Copper, mg/kg | 9 | 5 | 5 | 6 | 5 | 6 | 6 | 0 |
| Selenium, mg/kg | 0.09 | 0.65 | 0.43 | 0.44 | 0.87 | 0.23 | 0.50 | 0.27 |
| Zinc, mg/kg | 60 | 52 | 58 | 61 | 59 | 59 | 58 | −1 | the conventional canola meal is no doubt due to sodium added during conventional canola processing.

Example 6

Processing of ECM at POS Pilot Plant in Saskatoon, Canada to Simulate Commercial Processing In preparation for animal feeding evaluation of ECM, it was determined that the canola meal samples should be prepared under commercial processing conditions, given the effect of processing on nutritional value. Consequently samples were processed at the POS Pilot Plant in Saskatoon. Two processing conditions were used: a regular temperature (HT) in the desolventizer/toaster and a lower temperature (LT), in order to ensure that processing conditions did not exert over-riding influence on nutritional value. The processing conditions used at POS are outlined in Example 2.

TABLE 3

Nutrient composition of ECM and conventional canola meal prepared under simulated commercial processing conditions at the POS Pilot Plant in Saskatoon, Canada. (Analyses conducted at Universities of Illinois and Missouri).

| Component, % as is | 44864 (2010) LT | Canola meal LT | Canola meal HT |
|---|---|---|---|
| Dry matter | 90.2 | 90.3 | 88.4 |
| Crude protein | 44.7 | 37.0 | 36.0 |
| Fat | 3.3 | 3.3 | 3.6 |
| Ash | 7.9 | 6.7 | 6.5 |
| Sugars & Sucrose | 6.9 | 7.1 | 6.7 |
| Oligosaccharides | 0.45 | 1.57 | 1.55 |
| NDF | 20.8 | 27.0 | 28.1 |
| ADF | 13.8 | 19.2 | 19.0 |
| Lignin & polyphenols | 4.2 | 8.2 | 8.2 |

TABLE 3-continued

Nutrient composition of ECM and conventional canola meal prepared under simulated commercial processing conditions at the POS Pilot Plant in Saskatoon, Canada. (Analyses conducted at Universities of Illinois and Missouri).

| Component, % as is | 44864 (2010) LT | Canola meal LT | Canola meal HT |
|---|---|---|---|
| Phosphorus | 1.43 | 1.11 | 1.06 |
| Lysine | 2.41 | 2.10 | 2.01 |
| Methionine | 0.83 | 0.72 | 0.69 |
| Threonine | 1.69 | 1.47 | 1.42 |
| Tryptophan | 0.61 | 0.47 | 0.45 |

The pilot-processed meals showed a similar composition to the whole seed and Indianapolis white flake samples, and the differences between the ECM sample and the conventional canola are consistent with the analysis described in Table 2a and 2b: 7% points higher protein, 5% points lower ADF, 4% points lower lignin & polyphenols and 0.35% points higher phosphorus.

Example 7

Complete Analysis of Unprocessed ECM and Conventional Canola Seed

Nutrient composition of unprocessed canola seed. Five whole-seed samples of ECM lines from 2010 and 2011 production were analyzed at the University of Manitoba. These were compared with the official Canadian Grain Commission (CGC) composite seed sample for 2011 production, which by definition is the average quality of current commercial canola varieties being grown in western Canada during that season. The nutrient composition results are expressed on an oil-free, dry matter basis and shown in Table 4a and 4b.

TABLE 4a

Nutrient composition of ECM seed samples compared with conventional canola seed.

| Component, % DM, oil free | 44864 (2010) | 44864 (2011) | 121460 (2011) | 121466 (2011) | 65620 (2011) | CGC comp (2011) | ECM average | ECM – CGC comp |
|---|---|---|---|---|---|---|---|---|
| Crude protein | 52.2 | 51.5 | 50.3 | 51.4 | 50.2 | 43.9 | 51.1 | 7.2 |
| Ash | 9.1 | 9.2 | 8.2 | 8.3 | 7.8 | 7.8 | 8.5 | 0.7 |
| Simple sugars | 1.8 | 0.4 | 0.1 | 0.1 | 0.2 | 0.5 | 0.5 | 0.0 |
| Sucrose | 5.7 | 6.4 | 5.8 | 5.2 | 6.5 | 7.1 | 5.9 | −1.2 |
| Oligosaccharides | 0.6 | 3.3 | 3.1 | 3.3 | 3.6 | 3.5 | 2.8 | −0.7 |
| Starch | 0.2 | 0.3 | 0.2 | 0.3 | 0.3 | 0.3 | 0.3 | 0.0 |
| NDF | 23.1 | 20.7 | 21.9 | 23.1 | 20.7 | 27.2 | 21.9 | −5.3 |
| ADF | 15.4 | 14.2 | 15.8 | 17.8 | 13.7 | 21.0 | 15.4 | −5.6 |
| Total fiber | 30.9 | 28.6 | 30.1 | 29.6 | 29.4 | 32.5 | 29.7 | −2.8 |
| NSP | 21.7 | 21.0 | 21.3 | 19.2 | 22.1 | 21.6 | 21.1 | −0.5 |
| Lignin & polyphenols | 4.7 | 4.1 | 5.0 | 6.4 | 3.7 | 6.8 | 4.8 | −2.0 |
| Glycoprotein | 4.4 | 3.5 | 3.8 | 3.9 | 3.6 | 4.2 | 3.9 | −0.3 |
| Cellulose | 6.8 | 4.8 | 5.8 | 4.8 | 5.6 | 6.2 | 5.6 | −0.6 |
| ADF residue, (ADF-lignin-cellulose) | 3.8 | 5.3 | 5.1 | 6.6 | 4.4 | 8.0 | 5.0 | −3.0 |
| Hemi-cellulose (NDF-ADF) | 7.7 | 6.5 | 6.2 | 5.3 | 7.0 | 6.2 | 6.5 | 0.4 |
| Dietary fiber (NSP + lignin) | 26.5 | 25.0 | 26.3 | 25.6 | 25.9 | 28.4 | 25.8 | −2.5 |
| Phosphorus | 1.6 | 1.4 | 1.4 | 1.5 | 1.3 | 1.1 | 1.4 | 0.3 |
| Phytate Phosphorus | 0.8 | 0.7 | 0.8 | 0.8 | 0.6 | 0.6 | 0.7 | 0.1 |
| Non Phytate Phos | 0.8 | 0.7 | 0.6 | 0.8 | 0.7 | 0.5 | 0.7 | 0.2 |
| Crude protein, 3% oil, 88% DM | | | | | | 37.4 | 43.5 | 6.1 |

The results show that the greatest difference between ECM and conventional canola is higher protein content. ECM is 7.2% points higher in protein content (51.1% vs 43.9%) on an oil-free dry matter basis and 6.1% points higher (43.5% vs 37.4%) on a 3% oil, 88% dry matter basis (typical specification basis for commercial canola meal). See Table 4a, 4b. The higher protein appears to be accounted for by 2% lower lignin and polyphenols in the ECM and 3% lower ADF residue (ADF—lignin/polyphenols—cellulose). The ADF residue is likely a combination of glycoprotein and hemi-cellulose components. The fiber components are mainly found in the cell walls and hull. The phosphorus content of ECM is almost 30% higher than in conventional canola, and it appears evenly distributed between phytate and non-phytate forms. Phosphorus is a valuable nutrient in animal feeds and even though phytate-bound phosphorus is not well digested by poultry and swine, the common use of phytase enzyme in animal feeds will make this phosphorus available to the animal. Table 4b provides a similar comparison of amino acid composition in whole seed samples.

TABLE 4b

Amino acid composition (% of crude protein) of ECM seed samples compared with conventional canola seed.

| Component, % DM, oil free, % of CP | 44864 (2010) | 44864 (2011) | 121460 (2011) | 121466 (2011) | 65620 (2011) | CGC comp (2011) | ECM average | ECM − CGC comp |
|---|---|---|---|---|---|---|---|---|
| Crude protein | 52.2 | 51.5 | 50.3 | 51.4 | 50.2 | 43.9 | 51.1 | 7.2 |
| Essential amino acids | | | | | | | | |
| Arginine | 5.30 | 5.94 | 6.18 | 6.14 | 5.91 | 5.89 | 5.89 | 0.01 |
| Histidine | 2.90 | 3.03 | 3.02 | 2.94 | 3.02 | 3.12 | 2.98 | −0.14 |
| Isoleucine | 2.87 | 3.26 | 3.51 | 3.55 | 3.20 | 3.23 | 3.28 | 0.05 |
| Leucine | 5.82 | 6.36 | 6.73 | 6.68 | 6.33 | 6.48 | 6.38 | −0.10 |
| Lysine | 5.08 | 5.74 | 5.49 | 5.39 | 5.62 | 5.80 | 5.46 | −0.34* |
| Methionine | 1.71 | 1.91 | 1.81 | 1.78 | 1.75 | 1.80 | 1.79 | −0.01* |
| Phenylalanine | 3.31 | 3.63 | 3.86 | 3.83 | 3.66 | 3.68 | 3.66 | −0.02 |
| Threonine | 3.82 | 4.10 | 4.33 | 4.23 | 4.25 | 4.41 | 4.15 | −0.27* |
| Tryptophan | — | — | — | — | — | — | — | — |
| Valine | 3.98 | 4.51 | 4.75 | 4.76 | 4.32 | 4.42 | 4.46 | 0.05 |
| Non-essential aa | | | | | | | | |
| Alanine | 3.59 | 3.68 | 3.97 | 3.87 | 3.83 | 4.00 | 3.79 | −0.21 |
| Aspartic acid | 6.71 | 6.58 | 7.51 | 7.39 | 6.88 | 7.12 | 7.01 | −0.10 |
| Cystine | 2.21 | 2.42 | 2.16 | 2.14 | 2.33 | 2.16 | 2.25 | 0.09 |
| Glutamic acid | 16.09 | 18.23 | 18.02 | 17.84 | 17.73 | 17.64 | 17.58 | −0.06 |
| Glycine | 4.29 | 4.72 | 4.97 | 4.90 | 4.79 | 4.93 | 4.74 | −0.19 |
| Proline | 6.01 | 6.40 | 6.39 | 6.28 | 6.34 | 6.26 | 6.28 | 0.03 |
| Serine | 4.06 | 4.30 | 4.52 | 4.39 | 4.51 | 4.57 | 4.36 | −0.21 |
| Tyrosine | 2.23 | 2.35 | 2.56 | 2.59 | 2.50 | 2.60 | 2.45 | −0.15 |

*Regarded as main limiting essential amino acids in poultry and swine feeds

The results in Table 4b show that the amino acid composition (as a percentage of crude protein) is similar between ECM and commercial canola meal. This indicates that as protein has increased in the ECM lines, so have the important amino acids.

Example 8

Poultry TME and Amino Acid Digestibility

The true metabolizable energy (TME) and true available amino acid (TAAA) assays were developed in 1976 and 1981, respectively, by Dr. Ian Sibbald of Agriculture Canada in Ottawa. Due to the direct and non-destructive nature of the assays, the assays have become the methods of choice for determining the availability of energy and amino acids in poultry feed ingredients in much of the world, including the US.

Mature single comb white leghorn (SCWL) cockerels were used as the experimental animal of choice in separate studies conducted at the University of Illinois and the University of Georgia. It is well known that birds have a rapid gut-clearance time. By removing feed for a period of 24 hours, it is reliably assumed that the digestive tract of the test subjects are empty of previously consumed food residues.

Each bird (generally 8 individuals per treatment) is precision fed 35 grams of the test feed, placed directly into the crop via intubation. Ingredients that are high in fiber are usually fed at 25 instead of 35 grams, the spatial volume being similar. Following intubation, birds are provided access to water, but not to additional feed, for a period of 40 hours, during which time excreta are quantitatively collected. Following collection, excreta is dried in a forced air oven, usually at 80 C. It is subsequently weighed and ground for determination of gross energy (GE) in TME assays, or to determine amino acid content. The GE and amino acid composition of the ingredients are determined similarly. Once weighed, excreta samples are generally pooled and homogenized for a single GE or amino acid determination. Mass of excreta per bird varies much more than the GE or amino acid composition of the specific excreta. This observation, and the expense and time delay of GE and amino acid determinations, justifies pooling.

Digestibility is calculated using methods well known in the art for energy or for each amino acid individually. Estimates of endogenous loss of GE and amino acids are used to correct for experimental artifacts.

Example 9

Swine Digestible Energy (DE), Metabolizable Energy (ME)

DE and ME. Forty-eight growing barrows (initial BW: 20 kg) will be allotted to a randomized complete block design study at the University of Illinois. Pigs will be assigned 1 of 6 diets, with 8 replicate pigs per diet. Pigs will be placed in metabolism cages that will be equipped with a feeder and nipple drinker, fully slatted floors, a screen floor, and urine trays. This will allow for total, but separate, collection of urine and fecal materials from each pig.

The quantity of feed provided daily per pig will be calculated as 3 times the estimated requirement for maintenance energy (i.e., 106 kcal ME per $kg^{0.75}$; NRC, 1998) for the smallest pig in each replicate and divided into 2 equal meals. NRC 1998, Nutrient requirements of swine, Tenth Revised Edition. National Academy Press. Washington, D.C. Water will be available at all times. The experiment will last 14 days. The initial 5 days will be considered an adaptation period to the diet, with urine and fecal materials collected during the following 5 days according to standard procedures using the marker to marker approach (Adeola, O. 2001, Digestion and balance techniques in pigs, pages 903-916 in Swine Nutrition. $2^{nd}$ ed. A. J. Lewis and L. L. Southern, ed. CRC Press, New York, N.Y. NRC. 1998. Nutrient Requirements of Swine. $10^{th}$ rev. ed. Natl. Acad. Press, Washington D.C.). Urine samples will be collected in urine buckets over a preservative of 50 mL of hydrochloric acid. Fecal samples and 10% of the collected urine will be stored at −20° C. immediately after collection. At the conclusion of the experiment, urine samples will be thawed and mixed within animal and diet, and a sub-sample will be taken for chemical analysis.

Fecal samples will be dried in a forced air oven and finely ground prior to analysis. Fecal, urine, and feed samples will be analyzed in duplicate for DM and gross energy using bomb calorimetry (Parr Instruments, Moline, Ill.). Following chemical analysis, total tract digestibility values will be calculated for energy in each diet using procedures previously described (Widmer, M. R., L. M. McGinnis, and H. H. Stein. 2007. Energy, phosphorus, and amino acid digestibility of high-protein distillers dried grains and corn germ fed to growing pigs. J. Anim. Sci. 85:2994-3003.). The amount of energy lost in the feces and in the urine, respectively, will be calculated, and the quantities of DE and ME in each of the 24 diets will be calculated (Widmer et al., 2007). The DE and ME in corn will be calculated by dividing the DE and ME values for the corn diet by the inclusion rate of corn in this diet. These values will then be used to calculate the contribution from corn to the DE and ME in the corn-canola meal diets and in the corn-soybean meal diet, and the DE and ME in each source of canola meal and in the soybean meal sample will then be calculated by difference as previously described (Widmer et al., 2007).

Data will be analyzed using the Proc Mixed Procedure in SAS (SAS Institute Inc., Cary, N.C.). Data obtained for each diet and for each ingredient will be compared using an ANOVA. Homogeneity of the variances will be confirmed using the UNIVARIATE procedure in Proc Mixed. Diet or ingredient will be the fixed effect and pig and replicate will be random effects. Least squares means will be calculated using an LSD test and means will be separated using the pdiff statement in Proc Mixed. The pig will be the experimental unit for all calculations and an alpha level of 0.05 will be used to assess significance among means.

Example 10

Swine Amino Acid Digestibility (AID & SID)

Swine AID and SID were analyzed in a study at the University of Illinois. Twelve growing barrows (initial BW: 34.0±1.41 kg) were fitted with a T-cannula near the distal ileum and allotted to a repeated 6×6 Latin square design with 6 diets and 6 periods in each square. Pigs were housed individually in 1.2×1.5 m pens in an environmentally controlled room. Pens had solid sidings, fully slatted floors, and a feeder and a nipple drinker were installed in each of the pens.

Six diets were prepared. Five diets were based on cornstarch, sugar, and SBM or canola meal, and SBM or canola meal were the only sources of AA in these diets. The last diet was a N-free diet that was used to estimate the basal ileal endogenous losses of CP and AA. Vitamins and minerals were included in all diets to meet or exceed current requirement estimates for growing pigs (NRC, 1998). All diets also contained 0.4% chromic oxide as an indigestible marker.

Pig weights were recorded at the beginning and end of each period, and the amount of feed supplied each day was also recorded. All pigs were fed at a level of 2.5 times the daily maintenance energy requirement, and water was available at all times throughout the experiment. The initial 5 days of each period was considered an adaptation period to the diet. Heal digesta samples were collected for 8 hours on day 6 and 7 using standard procedures. A plastic bag was attached to the cannula barrel using a cable tie, and digesta flowing into the bag were collected. Bags were removed whenever they were filled with digesta, or at least every 30 min, and immediately frozen at −20° C. to prevent bacterial degradation of the amino acid in the digesta. On the completion of one experimental period, animals were deprived of feed overnight and the following morning, and a new experimental diet was offered.

At the conclusion of the experiment, ileal samples were thawed, pooled within animal and diet, and a subsample was collected for chemical analysis. A sample of each diet and of each of the samples of canola meal and SBM was collected as well. Digesta samples were lyophilized and finely ground prior to chemical analysis. All samples of diets and digesta were analyzed for DM, chromium, crude protein, and AA and canola meal and SBM were analyzed for crude protein and AA.

Values for apparent ileal digestibility (AID) of AA in each diet were calculated using equation [1]:

$$AID, (\%) = [1 - (AAd/AAf) \times (Crf/Crd)] \times 100, \quad [1]$$

where AID is the apparent ileal digestibility value of an AA (%), AAd is the concentration of that AA in the ileal digesta DM, AAf is the AA concentration of that AA in the feed DM, Crf is the chromium concentration in the feed DM, and Crd is the chromium concentration in the ileal digesta DM. The AID for CP will also be calculated using this equation.

The basal endogenous flow to the distal ileum of each AA was determined based on the flow obtained after feeding the N-free diet using equation [2]:

$$IAA_{end} = AAd \times (Crf/Crd) \quad [2]$$

where $IAA_{end}$ is the basal endogenous loss of an AA (mg per kg DMI). The basal endogenous loss of CP will be determined using the same equation.

By correcting the AID for the IAA$_{end}$ of each AA, standardized ileal AA digestibility values were calculated using equation [3]:

$$SID, (\%) = AID + [(IAA_{end}/AA_f) \times 100] \quad [3]$$

where SID is the standardized ileal digestibility value (%).

Data were analyzed using the Proc GLM procedure of SAS (SAS inst. Inc., Cary, N.C.). The 5 diets containing canola meal or SBM were compared using an ANOVA with canola meal source, pigs, and period as the main effects. A LSD test was used to separate the means. An alpha level of 0.05 was used to assess significance among means. The individual pig was the experimental unit for all analyses.

Example 11

Dairy AA Degradability

Amino acid degradability of ECM will be be assessed by in-situ incubation of samples of ECM meal in rumen-cannulated animals, such as dairy cattle, to estimate soluble and degradable protein contents and determine the rate of degradation (Kd) of the degradable fraction.

Cattle will be fed a mixed diet as a total mixed ration (TMR) containing 28.1% corn silage, 13.0% alfalfa silage, 7.4% alfalfa hay, 20.4% ground corn, 14.8% wet brewer's grains, 5.6% whole cottonseed, 3.7% soy hulls, and 7.0% supplement (protein, minerals, vitamins). Standard polyester in situ bags (R510, 5 cm×10 cm, 50-micron pore size) containing approximately 6 g dry matter (DM) of soybean meal (SBM), conventional canola meal (CM), or enhanced canola meal (ECM) will be incubated in the rumen for 0, 2, 4, 8, 12, 16, 20, 24, 32, 40, 48, and 64 hours. Duplicate bags will be removed at each time point and washed in tap water until the outflow is clear. Bags will be dried at 55° C. for 3 days and the residue will then be removed and weighed to determine dry matter (DM) disappearance. The residues will be analyzed for N content using the combustion method of Leco. Zero-time samples will not be incubated in the rumen, but will be washed and processed in the same manner as the rumen-incubated samples.

Samples of the zero-time residue and the residue remaining after 16 h of rumen incubation will be analyzed for proximate constituents (DM, crude fat, crude fiber, and ash) and amino acid (AA) composition (without tryptophan). These parameters may be used to generate estimates of rumen-degradable protein (RDP) and rumen-undegradable protein (RUP), as used in the National Research Council (2001) guidelines for nutrient requirements of dairy cattle.

The percentage of original sample N remaining at each time point may be calculated, and replicate values for each time point within cow averaged. Values from the three cows will be be fitted to the nonlinear equation described by Ørskov and McDonald (1979). In this approach, ruminal CP disappearance is assumed to follow first-order kinetics as defined by the equation, CP disappearance=A+B× $(1-e^{-Kd \times t})$, where A is the soluble CP fraction (% of CP), B is the potentially degradable CP fraction (% of CP), Kd is the degradation rate constant ($h^{-1}$), and t is the ruminal incubation time (h). Fraction C (not degradable in the rumen) is calculated as fraction A minus fraction B. Equations will be fitted using PROC NLIN of SAS (version 9.2; SAS Institute Inc., Cary, N.C.), with the Marquardt method of calculation.

The equations for computing RDP and RUP values (as percentages of CP) are: RDP=A+B[Kd/(Kd+Kp)], and RUP=B[Kp/(Kd+Kp)]+C, where Kp is the rate of passage from the rumen. Because passage rate cannot be calculated directly from these data (where the substrates are contained in the rumen and prevented from passing to the lower tract), a rate for Kp must be assumed. In this study, a value of 0.07 will be used for Kp, which is similar to the value calculated according to equations in NRC (2001) for a high-producing dairy cow consuming a typical lactation diet. Because the aim of this project is to compare protein sources and estimates of rumen degradability under the same conditions, the choice of a passage rate to determine RDP and RUP is arbitrary.

The final equation for each sample will be generated using samples incubated for 0, 2, 4, 8, 16, 24, and 48 h according to NRC (2001) recommendations. Data for the additional incubated time points in this study (i.e., 12, 20, 32, 40, and 64 h) may be used to verify the kinetics of the system and to ensure that the modified canola meal conforms to the assumptions in NRC (2001) specifications.

Example 12

Poultry TME and TAAA Including Comparison of Actual TME with Predicted TME Based on Analytical Results from the Universities of Illinois, Missouri and Manitoba Poultry True Metabolizable Energy (TME) evaluations on ECM samples were conducted at both the University of Illinois and the University of Georgia. The protocols are described in Example 8.

TABLE 5

TME content of ECM and conventional canola meal in studies at the University of Illinois and University of Georgia.

| Sample | TME, kcal/kg DM U of Illinois | TME, kcal/kg DM U of Georgia |
|---|---|---|
| POS Pilot plant prepared samples | n = 10 | n = 6 |
| 44864 (2010) ECM Low temp (LT) | 2524 a* (60)** | 2200 a (27) |
| Canola meal Low temp (LT) | 2320 b (59) | 1933 b (95) |
| Canola meal high temp (HT) | 2373 a, b (65) | 2048 a, b (99) |
| ECM LT - Canola meal LT | 204 (9%)*** | 267 (14%) |
| ECM white flake (WF) | | 2199 a (91) |
| Canola meal white flake (WF) | | 1899 b (51) |
| ECM WF - Canola meal WF | | 300 (16%) |
| Indianapolis White Flake samples | n = 5 | n = 6 |
| 44864 (2011) | 2460 f, g (85) | 2143 (46) |
| 121460 | 2353 g (97) | 2318 (81) |
| 121466 | 2635 f (92) | 2221 (99) |
| 65620 | 2611 f (99) | 2130 (44) |
| Soybean meal | 2913 (52) | 2790 (32) |

*means within a column and group with different letters are significantly different (p < .05)
**(SE)
***(percent difference)

In the case of the POS prepared ECM and canola meal samples, the appropriate comparison is between the two LT meals, in order to eliminate processing effects. The results were comparable in both the University of Illinois and University of Georgia studies. Poultry TME is significantly higher for the ECM (LT) than conventional canola meal (LT)-9% higher in the University of Illinois study and 14% higher in the University of Georgia study. These results confirm the prediction equation results below. Table 4.

White flake samples of ECM and conventional canola meals were also taken at POS immediately after the solvent extractor stage and before the DT stage. Poultry TME for these WF meals was compared in a separate study at the University of Georgia and, as with the LT samples, the ECM WF had significantly higher TME than the conventional canola meal WF. Table 4.

Four varieties of ECM were independently processed at the Dow AgroSciences laboratories in Indianapolis using the white flake process methods described in Example 3. These samples were then subjected to poultry TME analysis at the two universities. There was no significant difference in TME between the tested ECM lines, with the exception that the 121460 line appeared to have lower TME than the 121466 or 65620 lines.

Observed TME values from these studies were consistent with the following predicted metabolizable energy contents. The National Research Council Nutrient Requirements of Poultry (NRC, 1984, Nutrient requirements of poultry. Ninth Revised Edition. National Academy Press. Washington, D.C.)) has a prediction equation for ME in canola meal (double zero rapeseed meal):

$$ME\ kcal/kg = (32.76 \times CP\ \%) + (64.96 \times EE\ \%) + (13.24 \times NFE\ \%)$$

By calculation a 7% higher CP should be offset by a 7% lower NFE, so the net coefficient for CP should be: 32.76−13.24=19.52. This results in 137 kcal/kg more ME in ECM than in canola meal (7%×19.52=137). The problem with this equation is that NFE is a poor estimate of sugar and starch energy value.

An alternative equation is the EEC prediction equation for Poultry ME (adult). (Fisher, C and J. M. McNab. 1987. Techniques for determining the ME content of poultry feeds. In: Haresign and D. J. A. Cole (Eds), Recent Advances in Animal Nutrition—1987. Butterworths, London. P. 3-17):

$$ME, kcal/kg = (81.97 \times EE\ \%) + (37.05 \times CP\ \%) + (39.87 \times Starch\ \%) + (31.08 \times Sugars\ \%)$$

The EEC equation is a "positive contribution" equation which gives value to the digestible nutrients in canola meal, such as protein, fat, starch and free sugars. Since the only analytical difference between ECM and canola meal is protein, we can use the coefficient 37.05 to calculate the extra energy:

37.05×7%=259 kcal/kg. The EEC equation is designed for complete feeds, which generally have a higher digestibility than canola meal. Therefore, the 37.05 coefficient is too high.

An alternative approach is to use first principles for the energy value of protein. A rough estimate is 4 calories gross energy per gram of protein×80% protein digestibility×5% loss for nitrogen excretion=approximately 75% of gross calories per gram (3 calories of metabolizable energy per gram or 30× protein %. This yields a Metabolizable Energy of: 30×7%=210 kcal/kg extra ME in ECM.

In summary, it is expected that the ECM meal would have between 140-260 kcal/kg more poultry ME than conventional canola meal. The 140 kcal/kg value is likely grossly underestimated and the 260 kcal/kg may be on the high side. An increase of 200-220 kcal/kg more poultry ME is likely. Expressing this on an "as is" basis (Table 1), commercial ECM would likely have a poultry ME of 2200 kcal/kg versus 2000 kcal/kg for conventional canola meal. This is a 10% increase in energy.

Poultry true amino acid digestibility (TAAA) was also measured at both the University of Illinois and the Unviversity of Georgie. In this case, only POS-prepared meal samples were analyzed because the much higher amino acid digestibility of white flake versus toasted canola meal was not considered commercially relevant. Table 6.

TABLE 6

Poultry True Amino Acid Availability (TAAA) of key amino acids in ECM and conventional canola meals prepared at POS in studies.

| Amino Acid, TAAA % | University of Illinois ECM LT | University of Illinois CM LT | University of Illinois CM HT | University of Georgia ECM LT | University of Georgia CM LT | University of Georgia CM HT |
|---|---|---|---|---|---|---|
| Lysine | 81.8 | 79.6 | 76.6 | 86.8 | 83.5 | 82.9 |
| Methionine | 91.4 | 89.1 | 88.1 | 92.1 | 89.9 | 90.5 |
| Cystine | 80.2 | 82.8 | 79.8 | 79.6 | 80.7 | 78.1 |
| Threonine | 82.5 | 86.1 | 79.3 | 83.2 | 82.1 | 80.7 |
| Arginine | 88.9 | 90.0 | 89.6 | 89.8 | 85.0 | 89.0 |
| Tryptophan | 97.7 | 97.9 | 98.9 | 94.4 | 95.2 | 95.4 |

There were no statistically significant differences in poultry true amino acid availability between the different canola meal samples. Table 6.

Example 13

Swine Amino Acid Digestibility (AID and SID) and Predicted NE

Swine ileal amino acid digestibility studies were conducted at the University of Illinois. Meals prepared at the POS Pilot Plant were used for the comparison.

TABLE 7

Swine Apparent Ileal Amino Acid Digestibility (AID) and Swine Standardized Ileal Amino Acid Digestibility (SID) of protein and key amino acids in ECM and conventional canola meals prepared at POS in a study at the University of Illinois.

| Amino Acid, Digestible % | AID ECM LT | AID CM LT | AID CM HT | SID ECM LT | SID CM LT | SID CM HT |
|---|---|---|---|---|---|---|
| Crude Protein | 66.5 a* | 61.9 b | 63.9 a, b | 73.9 | 71.4 | 73.5 |
| Lysine | 73.0 a | 67.8 b | 67.9 b | 76.1 a | 71.6 b | 71.8 |
| Methionine | 81.2 | 80.0 | 79.4 | 83.0 | 81.6 | 82.3 |
| Cystine | 72.2 a, b | 71.1 b | 74.1 a | 74.9 b | 75.1 a, b | 77.8 a |
| Threonine | 63.1 | 61.0 | 63.6 | 69.4 | 68.6 | 71.0 |

TABLE 7-continued

Swine Apparent Ileal Amino Acid Digestibility (AID) and Swine Standardized Ileal Amino Acid Digestibility (SID) of protein and key amino acids in ECM and conventional canola meals prepared at POS in a study at the University of Illinois.

| Amino Acid, Digestible % | AID ECM LT | AID CM LT | AID CM HT | SID ECM LT | SID CM LT | SID CM HT |
|---|---|---|---|---|---|---|
| Arginine | 77.3 | 78.7 | 78.7 | 82.0 | 84.5 | 84.8 |
| Tryptophan | 81.1 a | 75.1 b | 78.4 a | 84.9 a | 80.7 b | 84.0 a |

*means within a row and group with different letters are significantly different (p < .05)

Some statistically significant differences in protein and amino acid digestibility between the ECM and canola meal samples were noted. The ECM had a higher crude protein AID than canola meal but the difference in protein SID was not significant. For both AID and SID, lysine is more digestible in the ECM than in conventional canola meal that has undergone the same heat treatment. Table 7.

For swine, the generally accepted equations to predict DE, ME, and NE in swine are those of Noblet as outlined in EvaPig (2008, Version 1.0. INRA, AFZ, Ajinomoto Eurolysine) and the NRC Nutrient Requirements of Swine (NRC, 1998, Nutrient requirements of swine; Tenth Revised Edition; National Academy Press. Washington, D.C.):

$$DE, kcal/kg = 4151 - (122 \times Ash \%) + (23 \times CP \%) + (38 \times EE \%) - (64 \times CF \%) \quad \text{Equation 1-4.}$$

$$NE, kcal/kg = 2790 + (41.22 \times EE \%) + (8.1 \times Starch \%) - (66.5 \times Ash \%) - (47.2 \times ADF \%) \quad \text{Equation 1-14.}$$

The Noblet equations are a hybrid of both positive and negative contribution factors: fat, protein and starch have positive coefficients, while ash, CF and ADF have negative coefficients. Protein is not used in the equation for Net Energy (NE), but the differences between ECM and canola meal can be captured by the differences in ADF. Since starch and ash are the same in ECM and canola meal, then the key difference is ADF. A 5% point lower ADF results in 47.2× 5%=236 kcal/kg more NE in ECM. This predicted number is similar to the poultry ME number, so again an increase in swine net energy of 200 kcal/kg for ECM on an "as is" basis (Table 1) is likely. This should result in an approximately 12% increase in energy.

Example 14

Additional ECM Hybrids

A new canola hybrid CL166102H also exhibited the enhanced meal (ECM) properties. Performance and quality traits measured on the seed of this hybrid, harvested from 2011 small plot trials, include oil, meal protein, ADF, and total glucosinolates (Tgluc). See Table 8.

The results in Table 8 clearly indicate that this new DAS ECM line is superior to the commercial variety with respect to meal attributes.

TABLE 8b

Agronomic performance of ECM lines (C3B03 Trials)

| Line | Oil (%) | Protein (%) | ADF (%) | Tgluc uM/G |
|---|---|---|---|---|
| CL166102 Hybrid | 49.4 | 49.9 | 12.8 | 10.6 |
| 5440 (129436) Commercial variety | 50.2 | 45.9 | 16.3 | 9.7 |

What is claimed is:

1. A dark canola seed comprising at least 45% crude protein content and not more than 18% acid detergent fiber as determined by reference chemistry on an oil-free dry matter basis, wherein the dark canola seed is selected from the group consisting of CL065620 (ATCC No. PTA-11697), CL044864 (ATCC No. PTA-11696), CL121460H (ATCC No. PTA-11698), CL166102H (ATCC No. PTA-12570), and CL121466H (ATCC No. PTA-11699).

2. The dark canola seed of claim 1, comprising at least 49.0% crude protein content on an oil-free, dry matter basis.

3. The dark canola seed of claim 1, comprising not more than 16% acid detergent fiber content on an oil-free, dry matter basis.

4. The dark canola seed of claim 1, further comprising a lignin and polyphenolic content of less than 6.8% on an oil-free dry matter basis.

5. The dark canola seed of claim 1, further comprising more than 1.1% phosphorous content on an oil-free dry matter basis.

6. A canola plant grown from the dark canola seed of claim 1.

7. The canola plant of claim 6, wherein the canola plant produces dark canola seed comprising a lignin and polyphenolic content of less than 6.8% on an oil-free dry matter basis.

8. The canola plant of claim 6, wherein the canola plant produces dark canola seed comprising more than 1.1% phosphorous content on an oil-free dry matter basis.

9. The canola plant of claim 6, wherein the canola plant produces dark canola seed comprising at least 43% oil.

10. The canola plant of claim 6, wherein the canola plant produces dark canola seed comprising an ADF level of less than about 18% or a polyphenolic level of less than about 5%.

11. A plurality of canola plants of claim 6, wherein the plurality of canola plants yield an average of at least 1700 kilograms of seed per hectare.

12. The canola plant of claim 6, wherein the plant is CL044864 (ATCC No. PTA-11696).

13. The canola plant of claim 6, wherein the plant is produced without genetic engineering or mutagenesis.

14. The canola plant of claim 6, wherein the canola plant produces dark canola seed comprising a phosphorous content of more than 1.3% on an oil-free, dry matter basis.

15. A dark canola seed produced by the canola plant of claim 6.

16. A canola plant grown from the dark canola seed of claim 15.

17. Canola meal produced from the dark seed of claim 1.

18. The canola meal of claim 17, wherein the canola meal has a poultry mean true metabolizable energy of at least 2200 kcal/kg.

19. The canola meal of claim 17, wherein the canola meal has a swine mean net energy of at least 1800 kcal/kg.

20. The canola meal of claim 17, wherein the canola meal has a favorable amino acid digestibility profile in swine, as compared to canola meal produced from a normal dark-seeded canola plant of the same species.

21. The canola meal of claim 17, wherein the canola meal has a favorable amino acid digestibility profile in poultry, as compared to canola meal produced from a normal dark-seeded canola plant of the same species.

22. The canola meal of claim 17, wherein said canola meal comprises an amino acid digestibility at least about 90% of that of soybean meal.

23. The canola meal of claim 17, wherein said canola meal comprises a digestible energy content or a metabolizable energy content at least about 80% of that of soybean meal.

24. A dark canola seed which is genetically stable for producing meal comprising at least 45% crude protein content, and not more than 18% acid detergent fiber as determined by reference chemistry on an oil-free, dry mass basis, wherein the canola seed is produced from an elite canola cultivar.

25. The canola seed of claim 24, further comprising at least 49.0% crude protein content on an oil-free, dry matter basis.

26. The canola seed of claim 24, further comprising not more than 16% acid detergent fiber content.

27. The canola seed of claim 24, wherein the canola seed is genetically stable for comprising at least one additional trait selected from the group consisting of an ADF level of less than about 18% or a polyphenolic level of less than about 5%.

28. The canola seed of claim 25, wherein the canola seed is genetically stable for comprising at least two additional traits selected from the group consisting of an ADF level of less than about 18% or a polyphenolic level of less than about 5%.

29. Canola meal produced from the dark seed of claim 24.

30. A method of introducing into a canola cultivar at least one desired trait selected from the group consisting of a protein level greater than about 45%, a phosphorus level of greater than about 1.2%, an ADF level of greater than about 18%, and a polyphenol level of greater than about 5%, in a seed coat color-independent manner, wherein the method comprises:
    crossing the canola plant of claim 6 with a plant of a second, different canola cultivar to produce $F_1$ progeny plants;
    selecting one or more progeny plants that have the desired trait(s) to produce selected progeny plants;
    backcrossing the selected progeny plants with the canola plant of claim 6 to produce backcross progeny plants;
    selecting for backcross progeny plants that have the desired trait(s) and physiological and morphological characteristics of the second, different canola cultivar to produce selected backcross progeny plants; and
    repeating the backcrossing and selection steps three or more times to produce inbred selected fourth or higher backcross progeny plants that comprise the desired trait(s).

31. The method according to claim 30, wherein the desired traits comprise protein level greater than about 45%, a phosphorus level of greater than about 1.2%, an ADF level of greater than about 18%, and a polyphenol level of greater than about 5%.

32. An enhanced canola meal obtainable directly from a dark canola seed, wherein the dark canola seed comprises at least 45% crude protein content and not more than about 18% acid detergent fiber, as determined by reference chemistry on an oil-free, dry matter basis, wherein the dark canola seed is selected from the group consisting of CL065620 (ATCC No. PTA-11697), CL044864 (ATCC No. PTA-11696), CL121460H (ATCC No. PTA-11698), CL166102H (ATCC No. PTA-12570), and CL121466H (ATCC No. PTA-11699).

33. The enhanced canola meal of claim 32, wherein the dark canola seed is genetically stable for comprising at least one additional trait selected from the group consisting of an ADF level of greater than about 18%, and a polyphenol level of greater than about 5%.

34. The enhanced canola meal of claim 32, wherein the dark canola seed is genetically stable for comprising a phosphorus level of greater than about 1.2% and a polyphenol level of greater than about 5%.

35. The enhanced canola meal of claim 32, wherein said enhanced canola meal may replace other, different, conventional canola meal or soybean meal as a protein or energy supplement in the diet of poultry, swine, or ruminants.

36. The canola plant of claim 6, wherein the plant is CL166102H (ATCC No. PTA-12570).

37. A canola plant selected from the group consisting of CL065620 (ATCC No. PTA-11697), CL044864 (ATCC No. PTA-11696), CL121460H (ATCC No. PTA-11698), CL166102H (ATCC No. PTA-12570), and CL121466H (ATCC No. PTA-11699).

* * * * *